United States Patent
Gho et al.

(10) Patent No.: US 9,084,830 B2
(45) Date of Patent: Jul. 21, 2015

(54) MICROVESICLES DERIVED FROM CELL PROTOPLAST AND USE THEREOF

(71) Applicant: AEON MEDIX INC., Pohang-si, Gyeongsangbuk-do (KR)

(72) Inventors: Yong Song Gho, Pohang-si (KR); Su Chul Jang, Yecheon-gun (KR); Yoon Keun Kim, Pohang-si (KR); Oh Youn Kim, Seoul (KR)

(73) Assignee: AEON MEDIX INC., Pohang-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/635,379

(22) Filed: Mar. 2, 2015

(65) Prior Publication Data

US 2015/0174271 A1    Jun. 25, 2015

Related U.S. Application Data

(62) Division of application No. 13/807,683, filed as application No. PCT/KR2011/004820 on Jun. 30, 2011.

(30) Foreign Application Priority Data

Jul. 1, 2010  (KR) .................. 10-2010-0063527
Jun. 30, 2011  (KR) .................. 10-2011-0065112

(51) Int. Cl.
*A61K 47/48* (2006.01)
*A61K 39/02* (2006.01)
*A61K 39/00* (2006.01)
*C07K 14/71* (2006.01)

(52) U.S. Cl.
CPC ....... *A61K 47/48838* (2013.01); *A61K 39/0011* (2013.01); *A61K 39/02* (2013.01); *C07K 14/71* (2013.01); *C07K 2319/00* (2013.01)

(58) Field of Classification Search
CPC .................. A61K 2039/55555; C12N 15/74
See application file for complete search history.

(56) References Cited

U.S. PATENT DOCUMENTS

| | | |
|---|---|---|
| 7,465,454 B2 | 12/2008 | Franzusoff et al. |
| 8,524,484 B2 | 9/2013 | Sabbadini et al. |
| 2003/0211086 A1 | 11/2003 | Berkley et al. |
| 2003/0224369 A1 | 12/2003 | Surber et al. |
| 2004/0110695 A1 | 6/2004 | Dobbie |
| 2005/0013913 A1 | 1/2005 | Lidster et al. |
| 2005/0147590 A1 | 7/2005 | Sabbadini et al. |

FOREIGN PATENT DOCUMENTS

| | | |
|---|---|---|
| JP | 2008-501336 A | 1/2008 |
| JP | 2010-514433 A | 5/2010 |
| WO | 2005079854 A1 | 9/2005 |

OTHER PUBLICATIONS

International Search Report issued for International Application No. PCT/KR2011/004820 dated Feb. 21, 2012.
B.G. Mersey et al., "The isolation of coated vesicles from protoplasts of soybean", Planta, vol. 163, pp. 317-327, 1985.
E.-Y. Lee et al., "Gram-positive bacteria produce membrane vesicles: Proteomics-based characterization of *Staphylococcus aureus*—derived membrane vesicles", Proteomics, vol. 9, pp. 5425-5436, 2009.
E.-Y. Lee et al., "Global proteomic profiling of native outer membrane vesicles derived from *Escherichia coli*", Proteomics, vol. 7, pp. 3143-3153, 2007.
R. Valenti et al., "Tumor-released microvesicles as vehicles of immunosuppression", Cancer Research, vol. 67, No. 7, pp. 2912-2915, Apr. 1, 2007.
E. Pap et al., "Highlights of a new type of intercellular communication: microvesicle-based information transfer", Inflammation Research, vol. 58, pp. 1-8, 2009.
T. Sugahara et al., "Preparation of cationic immunovesicles containing cationic peptide lipid for specific drug delivery to target cells", Cytotechnology, vol. 47, pp. 51-57, 2004.
Notice of Allowance dated Jan. 31, 2013 of corresponding Korean Patent Application No. 10-2011-0065112—5 pages.
Shingles, R et al, "Production of Membrane Vesicles by Extrusion: Size Distribution, Enzyme Activity, and Orientation of Plasma Membrane and Chloroplast Inner-Envelope Membrane Vesicles", Analytical Biochemistry, 1995, vol. 229, No. 1, pp. 92-98.
Office Action dated Jun. 4, 2014 of corresponding Japanese Patent Application No. 2013-518258—3 pages.
Giacalone et al. "Immunization with non-replicating *E. coli* minicells delivering both protein antigen and DNA portects mice from lethal challenge with *Lymphocytic choriomeningitis virus*," Vaccine 25(12), Mar. 8, 2007, 2279-2287.
Abbot, Alison "Medics braced for fresh superbug," Nature 436, p. 758 (2005).
Office Action dated Jan. 12, 2015 of corresponding Chinese Patent Application No. 201180033175.7—6 pages.

*Primary Examiner* — Karen Cochrane Carlson
(74) *Attorney, Agent, or Firm* — Knobbe, Martens, Olson & Bear, LLP

(57) ABSTRACT

The present application relates to microvesicles derived from a protoplast which is a bacterial, arhaea, fungal or plant cell or the like from which a cell wall is removed. The microvesicles derived from a protoplast enables free loading of a material necessary for diagnosis, treatment, vaccine, target induction, cell membrane fusion with a target cell, reduction of in vivo and in vitro side effects, stability improvement, and the like, and allows the therapeutic material, the diagnostic material and/or the vaccine material to be delivered specifically to a specific tissue or cell.

19 Claims, 35 Drawing Sheets

1. Intact Gram-negative bacteria
2. Gram-negative protoplast after lysozyme hydrolysis
3. Supernatnat with outer membrane and cell wall after lysozyme hydrolysis 1. microvesicles
2. Omp-loaded microvesicles
3. Omp-loaded microvesicles+Trypsin(500ug/ml)
4. (Lyzed Omp-loaded microvesicles)+Trypsin(500ug/ml)

☐ microvesicles
■ EGF receptor fusion protein-loaded microvesicles

MICROVESICLES DERIVED FROM CELL PROTOPLAST AND USE THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to a method of making a pharmaceutical composition comprising microvesicles derived from protoplasts of cells, such as bacteria, archaea, fungi, plant cells, and the like, and the use of thereof in the delivery of therapeutic, diagnostic, and/or vaccine substances to target cells and tissues.

BACKGROUND ART

For use in pharmacotherapy, a drug delivery system (DDS) is intended to aid the delivery of medicine to a target site within a body to bring about a therapeutic effect. If a medicine is excreted too fast from the body due to its low absorption or bioavailability rates, a DDS may be used to modify the drug release profile. Medicines with serious side effects need to be delivered to target tissues or cells only. For example, many currently available anticancer agents exhibit cytotoxicity on normal cells as well as on cancerous cells. The substantial delivery of anticancer agents to cancerous cells or tissues would reduce the agony and inconvenience of cancer patients during treatment.

Since the first use thereof in the 1960s, liposomes have been widely studied for their use in DDS. Advances in liposome research have constructed, in conjugation with polymers such as polyethylene glycol (PEG) studding the outside of the membrane, so-called stealth liposomes, which can avoid detection by the body's immune system. The PEG coating allows for longer circulatory half-life for the drug delivery mechanism. In practice, DOXIL, a pegylated liposome-encapsulated form of doxorubicin, has been developed. However, liposomes and stealth liposomes themselves cannot deliver drugs to target cells or tissues because they lack the ability to recognize the target cells or tissues. To allow liposomes to bind to a specific target, studies have recently been directed toward the impartment of targeting ligands, such as monoclonal antibodies, to liposomes, but none of them have yet passed clinical tests and been successfully commercialized.

In lieu of artificially synthesized liposomes consisting of lipids, naturally existing cellular membranes are used to develop delivery systems. A method of drug delivery using minicells secreted from microorganisms grown in drug-containing media is disclosed [WO 2005/079854, "Compositions and methods for targeted in vitro and in vivo drug delivery to mammalian cells via bacterially derived intact minicells"]. Minicells, usually comprised of bacterial cell membrane, are liable to contain toxic materials, for example, endotoxins (lipopolysaccharides) present in the outer membrane if derived from Gram-negative bacteria, or peptidoglycans present in the cell wall if derived from Gram-positive bacteria, so that they may cause various side effects such as systemic inflammation, sepsis, etc.

A protoplast is a bacterial, archaeal, fungal, plant cell that had its cell wall completely removed. The removal of the cell wall may resort to enzymes such as lysozyme for bacterial or archaeal cells, chitinase for fungal cells, and cellulase, pectinase and/or xylanase for plant cells. Protoplasts can be used to study membrane biology, including the uptake of macromolecules and viruses. In addition, protoplasts are applied to DNA transformation for making genetically modified organisms. Protoplasts may also be used for plant breeding, using a technique called protoplast fusion. However, microvesicles derived from protoplasts have not yet been reported, and neither has the applications thereof been, thus far.

SUMMARY

One aspect of the present invention relates to a method of making a pharmaceutical composition. The method may comprise providing bacteria comprising a cell wall, an antigenic protein and an extracellular domain, removing the cell wall from the bacteria to provide a cell-wall-deficient composition that is deficient of the cell wall and comprises the antigenic protein and the extracellular domain, processing the cell-wall-deficient composition to produce microvesicles comprising the antigenic protein and the extracellular domain, wherein the resulting microvesicles comprise a mixture of first type microvesicles with the extracellular domain on their outer surfaces and second type microvesicles with the extracellular domain on their inner surfaces, isolating, from the mixture, at least part of the first type microvesicles with the extracellular domain on their outer surfaces, and formulating a pharmaceutical composition comprising the isolated microvesicles with the extracellular domain on their outer surfaces.

In some embodiments, the bacteria may comprise Gram-positive bacteria. In some other embodiments, the bacteria may comprise Gram-negative bacteria.

In some other embodiments, the bacteria may comprise at least one selected from the group consisting of *Escherichia coli* and *Staphylococcus aureus*.

In still some other embodiments, the isolated microvesicles may comprise one or more non-native chemical entities chemically bonded to at least part of membrane components thereof, wherein the one or more non-native chemical entities are selected from the group consisting of a non-native molecule comprising a thiol (—SH) group, a non-native molecule comprising an amine (—NH$_2$) group, a non-native targeting molecule, a fusogen, and polyethylene glycol.

In still some other embodiments, the antigenic protein may be selected from the group consisting of a viral protein, a pathogenic bacterial protein and a cancer cell-derived protein.

In still some other embodiments, the viral protein may be from at least one virus selected from the group consisting of immunodeficiency virus (HIV), human papilloma virus (HPV), hepatitis B virus (HBV), hepatitis C virus (HCV) and influenza virus.

In still some other embodiments, the pathogenic bacterial protein may be from at least one bacterium selected from the group consisting of *Enterobacter aerogenes, Enterobacter cloacae, Staphylococcus aureus, Klebsiella pneumonia, Acinetobacter baumannii, Pseudomonas aeruginosa*, and *Enterococcus faecalis*.

In still some other embodiments, the pharmaceutical composition may further comprise at least one additional antigenic entity selected from the group consisting of a lipid molecule from a virus, a lipid molecule from a pathogenic bacteria, a carbohydrate molecule from a virus and a carbohydrate molecule from a pathogenic bacteria.

In still some other embodiments, the pharmaceutical composition may further comprise at least one of an immunopotentiator and an immunomodulator.

In still some other embodiments, the immunopotentiator may comprise one or more selected from the group consisting of double-stranded RNA (dsRNA), a cholera toxin, and alum.

In still some other embodiments, the immunomodulator may comprise one or more selected from the group consisting of interleukin (IL)-2, IL-4, IL-6, IL-12, IL-17, interferon gamma (IFN-gamma), vascular endothelial growth factor (VEGF), and fibroblast growth factor (FGF)-2.

In still some other embodiments, the pharmaceutical composition may further comprise at least one additional protein configured to target specific cells or tissues in the subject.

In still some other embodiments, the at least one additional protein may be selected from the group consisting of a cell adhesion molecule, an antibody, a targeting protein, a cell membrane fusion protein and any fusion proteins of two or more the foregoing.

In still some other embodiments, the at least one additional protein may be selected from the group consisting of a protein for ligand display, a peptide for ligand display, a protein for a ligand trap, a peptide for a ligand trap, and a fusion protein of two or more of the foregoing.

In still some other embodiments, the antigenic protein may comprise a non-native protein of the bacteria as the bacteria are transformed with a gene for encoding the antigenic protein.

In still some other embodiments, the antigenic protein and the extracellular domain may be connected to form a fusion protein, wherein the bacteria are transformed with a gene for encoding the fusion protein.

In still some other embodiments, the fusion protein may further comprise a cytoplasmic domain connected to the extracellular domain, wherein the first type microvesicles comprise the cytoplasmic domain on their inner surfaces and the second type microvesicles comprise the cytoplasmic domain on their outer surfaces, wherein isolating comprises adding, to the mixture, an antibody configured to bind with the cytoplasmic domain such that the second type microvesicles bind with the antibody, and removing the second type microvesicles bound with the antibody.

In still some other embodiments, the pharmaceutical composition comprises a vaccine composition for causing an immune response to the antigenic protein.

DETAILED DESCRIPTION OF EMBODIMENTS

Figure 1:
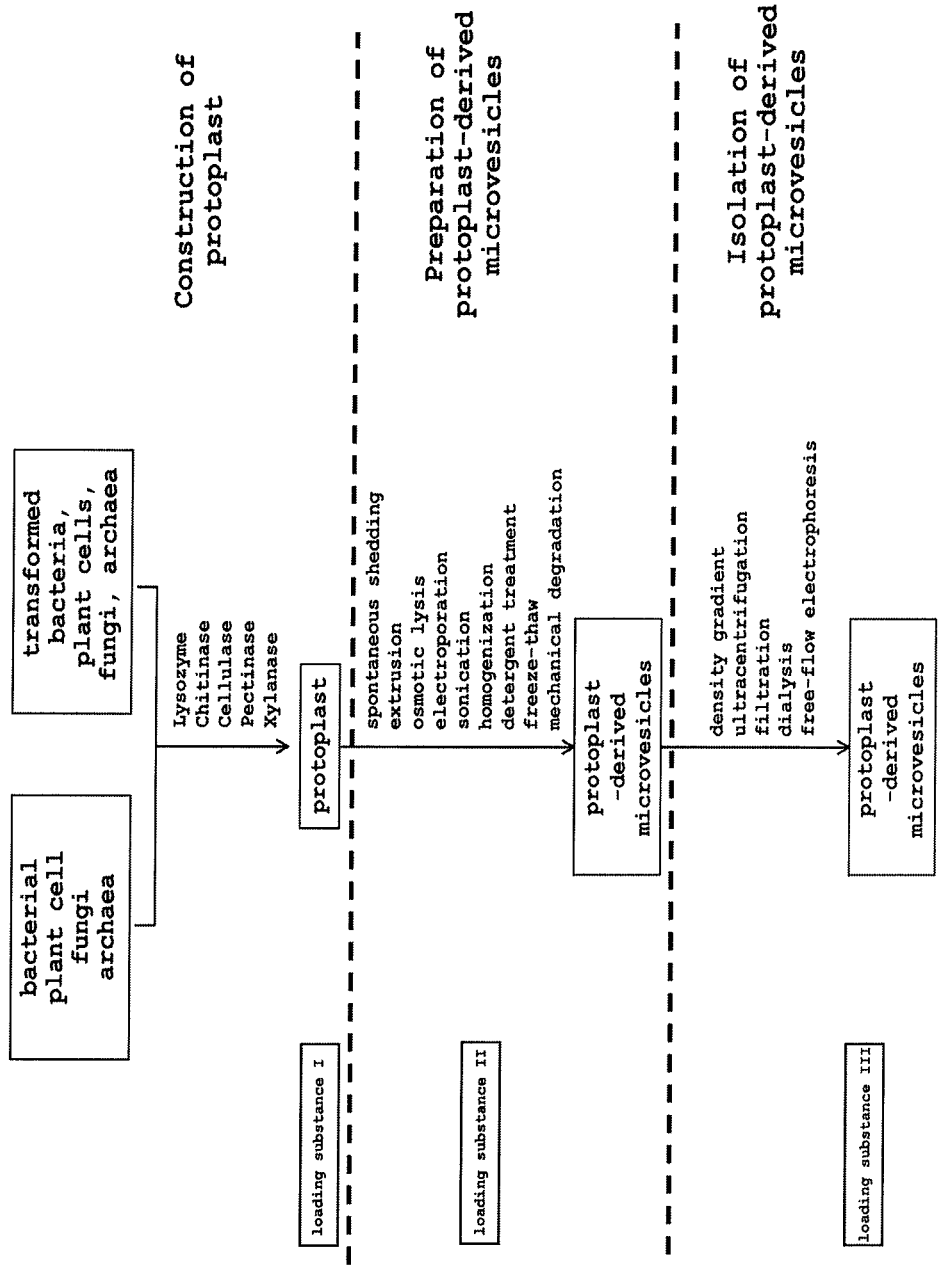
FIG. 1 is a schematic view illustrating processes of preparing protoplast-derived microvesicles.

Leading to the present invention, intensive and thorough research into DDS, conducted by the present inventors, aiming to overcome the problems encountered in the prior art, resulted in the finding that microvesicles derived from bacterial, archaeal, fungal, or plant cells that had their cell walls removed can be used to effectively deliver therapeutic and diagnostic substances, or vaccines, to specific cells or tissues.

It is therefore an aspect of the present invention to provide a composition comprising microvesicles derived from a cell protoplast. It is another aspect of the present invention to provide a pharmaceutical composition comprising microvesicles loaded with a substance necessary for diagnosis, therapy, vaccination, targeting, or cell membrane fusion with a target cell, and having a reduction in side effects and improvement in stability in vivo and in vitro. It is a further aspect of the present invention to provide a composition for the delivery of a therapeutic, a diagnostic, and/or a vaccine substance, comprising microvesicles derived from a cell protoplast. It is a still further aspect of the present invention to provide a method for delivering the substance to a specific target using the microvesicles, a substance delivery system comprising the microvesicles, and a kit for the diagnosis of a disease, comprising the microvesicles.

However, the technical aspects to be achieved in the present invention are not limited to those stated above, and other aspects may be clearly understood to those skilled in the art from the following description.

In accordance with an aspect thereof, the present invention provides a composition comprising microvesicles derived from a protoplast of a cell. The cell usable in certain embodiments of the present invention may be selected from the group consisting of a bacterial cell, an archaeal cell, a fungal cell, and a plant cell.

In accordance with another aspect thereof, the present invention provides a pharmaceutical composition comprising protoplast-derived microvesicles loaded with a therapeutic or diagnostic substance.

In accordance with a further aspect thereof, the present invention provides a pharmaceutical composition comprising protoplast microvesicles loaded with a vaccine substance.

Having the ability to transport a therapeutic, diagnostic, and/or vaccine substance to a specific tissue or cell, the microvesicles of certain embodiments of the present invention can be used to prevent, treat and/or diagnose a disease of interest. No particular limitations are imparted to the substance to be loaded into the microvesicles. The loading therapeutic, diagnostic, and/or vaccine substance may be expressed naturally or by transformation in the cell used as a source of the microvesicles, or may be introduced from the outside of the cell.

In accordance with a still further aspect thereof, the present invention provides a composition for the delivery of a composition for the delivery of a diagnostic, therapeutic and/or vaccine substance for a disease, comprising protoplast-derived microvesicles.

In accordance with still another aspect thereof, the present invention provides a delivery system of a diagnostic, therapeutic, and/or vaccine substance for a disease, comprising protoplast-derived microvesicles.

In accordance with yet another aspect thereof, the present invention provides a method for preparing protoplast-derived microvesicles, comprising: removing cell walls from cells to give protoplasts; constructing microvesicles in a suspension of the cells; and isolating the microvesicles from the suspension.

In accordance with a yet further aspect thereof, the present invention provides a method for preparing protoplast-derived microvesicles loaded with a therapeutic, a diagnostic, or a vaccine substance for a disease, comprising: externally loading the therapeutic, diagnostic, or vaccine substance into cells, followed by removing a cell wall from the cells to give protoplasts; constructing microvesicles in a suspension of the protoplast; and isolating the microvesicles from the suspension.

In accordance with yet still another aspect thereof, the present invention provides a method for preparing protoplast-derived microvesicles loaded with a therapeutic, a diagnostic, or a vaccine substance for a disease, comprising: removing a cell wall from cells to give protoplasts; externally loading the therapeutic, diagnostic, or vaccine substance into the protoplasts; constructing microvesicles in a suspension of the protoplasts loaded with the substance; and isolating the microvesicles from the suspension.

In accordance with a yet still further aspect thereof, the present invention provides a method for preparing protoplast-derived microvesicles loaded with a therapeutic, a diagnostic, or a vaccine substance for a disease, comprising: removing a cell wall from cells to give protoplasts; adding the therapeutic, diagnostic, or vaccine substance to a suspension of the protoplasts to construct a microvesicle; and isolating the microvesicles from the suspension.

In accordance with another additional aspect thereof, the present invention provides a method for preparing protoplast-derived microvesicles loaded with a therapeutic, a diagnostic, or a vaccine substance for a disease, comprising: removing a cell wall from cells to give protoplasts; constructing microvesicles in a suspension of the protoplasts; adding the therapeutic, diagnostic, or vaccine substance to the suspension comprising the microvesicles and allowing the therapeutic, diagnostic, or vaccine substance to be loaded into the microvesicle; and isolating the microvesicle loaded with the therapeutic, diagnostic, or vaccine substance from the suspension.

In accordance with a further additional aspect thereof, the present invention provides a method for preparing protoplast-derived microvesicles loaded with a therapeutic, a diagnostic, or a vaccine substance for a disease, comprising: removing a cell wall from cells to give protoplasts; constructing microvesicles in a suspension of the protoplasts; isolating the microvesicles from the suspension; and adding the therapeutic, diagnostic, or vaccine substance to the suspension containing the microvesicle, and allowing the therapeutic, diagnostic, or vaccine substance to be loaded into the microvesicle.

In accordance with still another additional aspect thereof, the present invention provides a method for the delivery of a diagnostic, therapeutic, or vaccine substance to a specific cell or tissue, comprising the use of protoplast-derived microvesicles loaded with the diagnostic, therapeutic, or vaccine substance.

In accordance with still a further additional aspect thereof, the present invention provides a method for the therapy and/or diagnosis of a disease, comprising delivering a diagnostic or therapeutic to a specific cell or tissue by use of protoplast-derived microvesicles loaded with the therapeutic or diagnostic substance.

In accordance with yet another additional aspect thereof, the present invention provides a method for the prophylaxis and/or therapy of a disease, comprising delivering a vaccine substance to a specific cell or tissue by use of protoplast-derived microvesicles loaded with the vaccine substance.

In accordance with a yet further additional aspect thereof, the present invention provides a kit for the diagnosis of a disease, comprising protoplast-derived, sub-protoplast sized, microvesicles loaded with a primer, a probe, an antisense nucleic acid, or an antibody necessary for the diagnosis of the disease.

The pathogenic capability of microbial or higher organism cells is often associated with certain components of cell envelopes and membranes, including endotoxins located in the cell outer membrane, and peptidoglycans and lipoproteins located in the cell wall in Gram-negative bacteria, pseudopeptidoglycan in archaea, and chitin and cellulose located in the cell wall in fungi and plant cells. These components may trigger immune responses with the concomitant production of serious symptoms. Being derived from protoplasts constructed by removing the cell wall from bacteria, archaea, fungi, or plant cells, the microvesicles of certain embodiments of the present invention do not trigger an immune response by themselves. Further, the protoplast-derived microvesicles are advantageous in that they can be readily loaded with a therapeutic and/or diagnostic substance, or a vaccine substance, and can be produced on a mass scale.

Therapeutic, diagnostic, and/or vaccine substances, if loaded to the protoplast-derived microvesicles of certain embodiments according to the present invention, can be delivered to target cells or tissues without being directed towards off-target cells or tissues. Accordingly, the protoplast-derived microvesicles according to some embodiments of the present invention can selectively deliver a therapeutic agent, such as a drug, to cells or tissues of interest, with a significant reduction in side effects, thus alleviating the patient's inconvenience and pain. In addition, thanks to the precise targeting capability thereof, the protoplast-derived microvesicles according to some embodiments of the present invention can be used to accurately diagnose diseases when they are loaded with a diagnostic substance, and to effectively vaccinate the subject when they are loaded with a vaccine substance, without causing side effects.

Moreover, if the microvesicles are derived from the protoplast of a cell expressing the therapeutic, the diagnostic, and/or the vaccine substance, they have industrial and economic advantages because they can be produced without purifying the substance.

Also, the microvesicles with therapeutic and/or diagnostic substances loaded thereto and the preparation method thereof in accordance with some embodiments of the present invention may be used for in vitro and/or in vivo treatment, diagnosis or experiments.

In accordance with an aspect thereof, the present invention addresses a composition comprising microvesicles derived from a protoplast of a cell.

Examples of the cell usable in certain embodiments of the present invention include bacteria with cell walls, archaea, fungi, plants cells, L-form bacteria (or cell wall-deficient (CWD) bacteria, but are not limited thereto. The bacteria may be Gram-positive or Gram-negative. For example, *Escherichia coli* (*E. coli*) and *Staphylococcus aureus* (*S. aureus*), which are Gram-negative and Gram-positive, respectively, may be used.

In addition, among the cells usable in some embodiments of the present invention are "naturally existing cells" and "transformed cells."

As used herein, the term "naturally existing cells" is intended to include cells that can be guided to specific cells or tissues, cells that express specific substances.

The term "transformed cells," as used herein, is intended to include, but is not limited to, cells that have been transformed to have reduced toxicity or inhibited synthesis of their cell wall; cells that have been transformed to express a substance necessary for diagnosis, therapy, vaccination, targeting, or cell membrane fusion with a target cell (fusogen); and a mixture thereof.

Further, the "transformed cells" include cells that have been transformed twice or more times, and cells that have been transformed in such a way that they are prevented from expressing a specific protein.

In one embodiment of the present invention, the transformed cells may be transformed to express a substance selected from the group consisting of a cell adhesion molecule, an antibody, a targeting protein, a fusogen, and a fusion protein thereof.

As for the "transformation of cells," it may be achieved by introducing a foreign gene into the cells, by treating the cells with a substance, or by applying a physical/chemical/biological/electrical/mechanical stimulus to the cells.

The term "protoplast," as used herein, refers to a bacterial, archaeal, fungal, or plant cell that had its cell wall completely or partially removed, with the lipid bilayer membrane thereof naked, and thus includes protoplasts, which have their cell wall entirely removed, spheroplasts, which have their cell wall only partially removed, and "L-form bacteria," but is not limited thereto.

The "L-form bacteria" include naturally existing cells and transformed cells, but are not limited thereto.

The term "protoplast-derived microvesicle," as used herein, is intended to refer to a sub-protoplast sized vesicle the interior of which is separated from the outside environment only by a lipid bilayer membrane composed of cell membrane lipids, membrane proteins and a cytoplasmic component.

Examples of the "protoplast-derived microvesicle" useful in certain embodiments of the present invention include, but are not limited to, those that are spontaneously secreted from protoplasts, those that are artificially synthesized from protoplasts using a physical, mechanical, electrical or chemical method, and those that are prepared by treatment with a specific substance or by transformation which induces the secretion of microvesicles from protoplasts.

In one embodiment of the present invention, the microvesicles may retain the same membrane topology as that of the plasma membrane serving as a source.

In another embodiment of the present invention, the microvesicles may include, but are not limited to, inclusion bodies.

In another embodiment of the present invention, the microvesicles may further comprise a component in their membrane other than that derived from the cell membrane of the protoplast serving as a source.

The component other than that derived from the cell membrane may include targeting molecules, fusogens, cyclodextrins, and polyethylene glycol, but is not limited thereto. In addition, the component other than that derived from the cell membrane may be added using a variety of methods, including chemical modification of cell membranes.

According to another embodiment of the present invention, membrane components of the microvesicles may be chemically modified. For example, they may be chemically modified with thiol (—SH) or amine (—$NH_2$) groups, or by binding a targeting molecule, a fusogen, or polyethylene glycol to the membrane.

Contemplated by the present invention in accordance with another aspect thereof is a pharmaceutical composition comprising microvesicles loaded with a substance necessary for diagnosis, therapy, vaccination, targeting, cell membrane fusion with a target cell, or reduction in side effects and improvement in stability in vivo and in vitro.

As used herein, "loading" a substance into the protoplast-derived microvesicles means that one or more substances necessary for diagnosis, therapy, vaccination, targeting, cell membrane fusion with a target cell, and/or reduction in side effects and improvement in stability in vivo and in vitro are displayed on the surface of the microvesicles or encapsulated within the microvesicles, but the present invention is not limited thereby.

The substance to be loaded into the protoplast-derived microvesicles may come from the cells (inclusive of naturally existing cells and transformed cells) serving as a source of the microvesicle. That is to say, the cells useful in some embodiments of the present invention include cells which naturally express a therapeutic, a diagnostic, or a vaccine substance or which are transformed to express the substance.

In one embodiment of the present invention, a cell which has been transformed to express a substance selected from the group consisting of, but not limited to, a cell adhesion molecule, an antibody, a targeting protein, a fusogen, and a fusion protein thereof may be used so as to load a targeting protein into the protoplast-derived microvesicle. The targeting protein may be displayed on or encapsulated within the protoplast-derived microvesicle.

The transformation of cells can be achieved by stimulating the cells or introducing a foreign gene into the cells to modify, e.g., upregulate or downregulate, the expression of proteins of interest. The introduction of a foreign gene may induce the expression or inhibition of a protein of interest.

In this context, plasmid DNA, RNA or virus is introduced into cells using calcium phosphate precipitation, lipofectamine mediation, electroporation, microinjection, or other methods known in the art. After protoplasts are transformed to express a protein or an antibody capable of binding to cancer cells, tissues or vessels or inflammatory tissues, solely or as a fusion protein on the surface thereof, microvesicles can be constructed from the cells.

To downregulate the expression of a protein of interest, miRNA, siRNA, or antisense RNA may be employed. When microvesicles constructed from the protoplast of a cell are directed toward two targets, the cell may be transformed in such a way that the expression of one or more specific proteins is inhibited to reduce the guidance of the cells to one of the two targets, meaning that the specificity in the delivery of the substance for microvesicles derived from the transformed cells is enhanced. Alternatively, cells which have undergone two or more rounds of transformation may be used. For example, primary transformants may be subjected to secondary transformation before being used as a source for protoplasts from which microvesicles are constructed.

There are a variety of plasma membrane proteins that are involved in the guidance of monocytes, macrophages, dendritic cells and stem cells to specific tissues. For example, cell adhesion molecules including integrins such as LFA-1 (leukocyte function-associated antigen-1) and Mac-1 (macrophage-1 antigen) are present on the surface of monocytes. These cell adhesion molecules can bind to other cell adhesion molecules, such as ICAM-1 (intercellular adhesion molecule-1) and VCAM-1 (vascular cell adhesion molecule-1), on vascular cells. Interaction between LFA-1 and ICAM-1 allows monocytes to pass through vascular endothelial cells so that the monocytes can be guided to inflammatory or cancerous tissues. When transformed to express plasma membrane proteins specific for cancer or tissues of interest, cells can be guided to various tissues including cancerous or inflammatory tissues. For example, the cell membrane protein ERBB2 is overexpressed on the surface of breast cancer cells. T cells can be allowed to target cancer cells by transformation to express modified T-cell receptors (TCR). T cells can be directed toward breast cancer tissue if they are transformed to express a fusion protein in which TCR is fused at its external domain to an antibody recognizing ERBB2 and at its cytoplasmic domain to CD3 ζ (zeta) responsible for intracellular signaling. Further, T cells can be guided toward large intestine cancer, pancreatic cancer and lung cancer tissue if they are transformed to express a fusion protein in which an antibody recognizing a carcinoembryonic antigen abundantly found in the cancer tissues is fused to CD3 ζ. The protoplast-derived microvesicles constructed from the cells that express the proteins or fusion proteins can be guided toward tissues of interest, but the targeting molecules are not limited to the above-illustrated proteins or fusion proteins.

In another embodiment of the present invention, the microvesicles may be prepared from a cell which is adapted to express a substance selected from the group consisting of a cytokine, a growth factor, a cell adhesion molecule, an antibody, a receptor, and a combination thereof.

The substance loadable to the protoplast-derived microvesicles may be not derived from the source cells, but is foreign to the cells. The loading substance may be homogenous or heterogeneous.

The microvesicles of some embodiments of the present invention may be loaded with a substance which is not derived from the source cells, but is foreign to the cells, using one of the following methods: loading the substance 1) directly into the cells; 2) after protoplasts are derived from the cells; 3) upon the construction of microvesicles; and 4) after the construction of protoplast-derived microvesicles.

Further, the substance may be loaded onto the surface of the microvesicles using, but not limited to, physical, chemical and/or biological methods.

In detail, various foreign substances may be loaded to the microvesicles of certain embodiments according to the present invention as follows.

First, microvesicles can be prepared from a cell which has already been loaded with various therapeutic, diagnostic, and/or vaccine substances of interest. For example, when cells are cultured in a medium containing the therapeutic or diagnostic substances of interest, they may contain the substances therein. Alternatively, the substance may be introduced into cells by electroporation. Microvesicles which spontaneously shed from or which are constructed from the cells containing the substances by ultrasonication, extrusion or mechanical degradation are loaded with the substance.

Next, microvesicles can be prepared from a protoplast which has already been loaded with various therapeutic, diagnostic, and/or vaccine substances of interest. For example, when protoplasts, after being converted from cells, are cultured in a medium containing the therapeutic or diagnostic substances of interest, they may contain the substances therein. Alternatively, the substance may be introduced into the protoplasts by electroporation. Microvesicles which spontaneously shed from or which are constructed from the protoplasts containing the substances by ultrasonication, extrusion or mechanical degradation are loaded with the substance.

On one hand, the substance may be loaded into microvesicles in the course of the construction thereof. For instance, when a suspension of protoplasts containing a substance of interest is extruded through a sub-protoplast size filter, microvesicles are formed, with the substance loaded thereto.

In another alternative, microvesicles may be loaded with a substance of interest after they are constructed or formed from protoplasts. For example, the loading can be achieved by incubating a suspension of microvesicles with the substance or by electroporating the substance into already prepared microvesicles.

However, it should be appreciated by those skilled in the art that the loading of a substance of interest into microvesicles is not limited to the above-illustrated methods.

Among the therapeutic and/or diagnostic substances loadable to the protoplast-derived microvesicles of some embodiments of the present invention are anticancer agents, anti-inflammatory agents, angiogenesis inhibitors, peptides, proteins, toxins, nucleic acids, beads, microparticles and nanoparticles, but the present invention is not limited thereby.

An anticancer agent is a generic term for a drug used to suppress the growth and metastasis of cancer. Most anticancer agents act to block the replication, transcription and/or translation of cancer cells. No particular limitations are imparted on kinds of the anticancer agents useful in the present invention. Under the general principle in which kinds of cancer cells, absorption rates of anticancer agents (the duration of treatment, the route of administration, etc.), positions of tumor, sizes of tumor, etc. are taken into consideration, anticancer agents may be selected. Examples of the anticancer agents useful in at least certain embodiments of the present invention include DNA alkylating agents, such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin, anti-cancer antibiotics, such as dactinomycin (actinomycin D), doxorubicin (adriamycin), epirubicin, idarubicin, mitoxantrone, plicamycin, mitomycin and C Bleomycin, and plant alkaloids, such as vincristine, vinblastine, paclitaxel, docetaxel, daunorubicin, taxol, oncovin, prednisone, cisplatin, herceptin, rituximab, etoposide, teniposide, topotecan and iridotecan. Also, radioactive substances known in the art may be used. However, the anticancer agents useful in certain embodiments of the present invention are not limited to the examples.

Further, the anti-inflammatory agent loadable to the protoplast-derived microvesicles of some embodiments of the present invention is selected from the group consisting of, but not limited to, dexamethasone, solumedrol, aspirin, indomethacin, ibuprofen, clobetasol propionate, diflorasone diacetate, halobetasol propionate, amcinonide, fluocinonide, mometasone furoate, desoximetasone, diclofenac, and piroxicam.

As used herein, the term "cancer" refers to a group of different diseases, which are characterized by unregulated cell growth and infiltration to neighboring tissues due to the disruption of programmed cell death. A target to be treated according to some embodiments of the present invention may be selected from a cancer selected from the group consisting of, but not limited to, carcinoma originating from epithelial cells, such as lung cancer, larynx cancer, stomach cancer, large intestine/rectal cancer, liver cancer, gallbladder cancer, pancreatic cancer, breast cancer, uterine cervical cancer, prostate cancer, kidney cancer, skin cancer, etc., sarcoma originating from connective tissue cells, such as bone cancer, muscle cancer, fat cancer, fibrous cell cancers, etc., blood cancer originating from hematopoietic cells, such as leukemia, lymphoma, multiple myeloma, etc., and neuroma, a tumor of nervous tissues.

As used herein, the term "vascular disease" refers to a group of different diseases in which dysfunction is generated within blood vessels or in vessel walls due to metabolic, infectious, toxic or immune causes. A target to be treated according to some embodiments of the present invention may be selected from a vascular disease selected from the group consisting of, but not limited to, arteriosclerosis (or atherosclerosis), angina pectoris, acute myocardial infarction, stroke, vascular dementia, metabolic vascular diseases, such as ischemic vascular diseases, and infectious, toxic or immune vascular diseases such as sepsis, disseminated intravascular coagulation, thrombotic embolism, vasculitis, nephritis, acute respiratory distress syndrome, emphysema, etc.

The term "inflammation," as used herein, refers to a syndrome or symptom including edema, resulting from an abnormal accumulation of body fluid in tissues, congestion due to vascular dilation, increased heat by pyrogen and vasodilatation, and pain induced by arachionic acid metabolites. Inflammation may be classified as acute, sub-acute, and chronic inflammation according to time, and as infectious, allergic, auto-immune, toxic, metabolic and traumatic inflammatory diseases according to pathophysiological conditions. A target to be treated according to some embodiments of the present invention may be selected from the group consisting of, but not limited to, respiratory inflammatory diseases such as rhinitis, sinusitis, otitis media, rhinopharyngitis, laryngitis, bronchitis, asthma, chronic obstructive pulmonary disease, bronchiectasis, bronchiolitis, pneumonia, pulmonary fibrosis, etc., inflammatory diseases of the digestive system such as stomatitis, esophagitis, gastritis, peptic ulcer, irritable bowel syndrome, ulcerative colitis, cholecystitis, cholangitis, pancreatitis, hepatitis, etc., skin inflammation such as atopic dermatitis, psoriasis, etc., cardiovascular inflammatory diseases such as endocarditis, myocarditis, pericarditis, vasculitis, arteriosclerosis, sepsis, etc., inflammatory diseases of the endocrine system, such as thyroiditis, parathyroiditis, diabetes, etc., inflammatory diseases of the urogenital system such as nephritis, nephropathy, interstitial nephritis, orchitis, oophoritis, endometritis, vaginosis, etc., inflammatory diseases of the musculoskeletal system, such as rheumatoid arthritis, spondylarthritis, osteoarthritis, gout, systemic lupus ethematosus, systemic sclerosis, myopathy, Sjogren syndrome, and Behçet's disease, and inflammatory diseases of the neuropsychiatric system, such as vascular dementia, Alzheimer's disease, neurodegenerative disease, depressive disorder, schizophrenia, etc.

As used herein, the term "angiogenesis inhibitor" refers to a drug that functions to suppress the growth of new blood vessels from preexisting vessels. Most angiogenesis inhibitors have the function of suppressing the growth and metastasis of cancer, and inflammatory reactions. No particular limitations are imparted to the kinds of the angiogenesis inhibitors available as the therapeutic substance of at least some embodiments of the present invention.

The therapeutic or diagnostic substance loaded to the protoplast-derived microvesicles of some embodiments of the present invention may include proteins or peptides. By way of examples, growth factors, such as VEGF (vascular endothelial growth factor) and EGF (epidermal growth factor), cytokines, such as IL-1 (interleukin-1), interferon (IFN)-gamma and IL-10, antibody therapeutics, DNase, and various proteins or peptides suppressing the growth and metastasis of cancer cells and inflammatory responses may be employed without limitations.

The proteins or peptides may be expressed within cells or displayed on plasma membranes. Also, their entirety or active sites may be expressed solely or as fusion proteins. It is known that the activity of proteins or peptides displayed on plasma membranes is higher than when they are expressed within cells as a result of the higher local concentration. Accordingly, proteins or peptides loaded on the surface of the microvesicles may act as ligand displays to trigger signaling, like cell adhesion molecules, growth factors, cytokines, fusions thereof, etc., or as ligand traps to inhibit the function of various ligands, like antibodies, receptors, or fusions thereof. However, proteins or peptides usable as ligand displays or traps in the present invention are not limited to the examples.

Also, the therapeutic or diagnostic substance loaded to the protoplast-derived microvesicles of some embodiments of the present invention may include toxins. The term "toxin" refers to a poisonous substance produced within living cells or organisms, which is capable of causing a disease on contact with or adsorption by body tissues. Using a toxin, cell death can be induced. No particular limitations are imparted to the kind of toxin available as the therapeutic substance of the present invention.

The nucleic acid loadable to the protoplast-derived microvesicles may be selected from the group consisting of DNA, RNA, aptamers, LNA (locked nucleic acid), PNA (peptide nucleic acid), and morpholinos. In detail, examples of the nucleic acid include DNA, miRNA, siRNA, antisense RNA, sense RNA, and nucleic acid homologs such as LNA, PNA, morpholino, etc., but are not limited thereto. These nucleic acids may be used to evoke sense effects, antisense effects, RNA interference, or inhibition of protein functions.

In some embodiments of the present invention, protoplast-derived microvesicles loaded with nucleic acids encoding fluorescent proteins or with various fluorescents can be used for diagnosis. When protoplast-derived microvesicles designed to target specific cells or tissues are loaded with a plasmid DNA carrying a gene encoding a fluorescent protein and are introduced into the body, the fluorescence signal emitted from the fluorescent protein makes it possible to recognize where the target cells or tissues exist. Likewise, fluorescent quantum dots or other various fluorescents may be loaded to protoplast-derived microvesicles and used to detect the position of specific cells and tissues within the body. That is, fluorescence generated from target cells or tissues can be used for diagnosis. In addition, fluorescence-emitting quantum dots may be applied to the treatment of diseases because they induce apoptosis.

Therapeutic or diagnostic substances other than fluorescents, loadable to protoplast-derived microvesicles, may be exemplified by microparticles or nanoparticles. Examples include iron oxide particles, gold particles and carbon nanotubes, but are not limited thereto. Magnetic beads may be used as the therapeutic or diagnostic substance and loaded to the microvesicles. Magnetic particles such as iron oxide may be used as an image contrasting agent for MRI. Moreover, nucleic acids or proteins conjugated with nanoparticles may be employed. Diagnostic radioactive substances are also available.

In accordance with a further aspect thereof, the present invention addresses a pharmaceutical composition comprising protoplast-derived microvesicles loaded with a vaccine substance.

Examples of the vaccine substance loadable to the protoplast-derived microvesicles of some embodiments of the present invention may include an antigen, an immunopotentiator, and an immunomodulator. Other various kinds of vaccine substances may be employed without limitations as well.

The antigen may be derived from viruses or bacteria and may be a protein antigen or a non-protein antigen, such as a lipid/carbohydrate. Also, the antigen may be a protein derived from specific cancer cells. The antigen may be homogenous or may be a combination of two or more different antigens. For example, two or more different bacterial antigens may be loaded to the microvesicles. Alternatively, a bacterial antigen, a cancer cell-derived antigen, and a viral antigen may be loaded simultaneously.

The bacterial antigen usable in certain embodiments of the present invention may be derived from, but not limited to, *enterobacter* species (*Enterobacter aerogenes* & *Enterobacter cloacae*), *Staphylococcus aureus, Klebsiella pneumonia, Acinetobacter baumannii, Pseudomonas aeruginosa*, and *Enterococcus faecalis*.

The viral antigen loadable to the microvesicles of certain embodiments of the present invention may be derived from, but not limited to, human immunodeficiency virus (HIV), human papiloma virus (HPV), hepatitis B virus (HBV), hepatitis C virus (HCV), or influenza virus.

In addition, the antigen may come from the cell itself, whether intact or transformed, which serves as a source from which the protoplast-derived microvesicles is constructed, or may be a substance that is foreign to the cell. For example, an entirety or a part of the component derived from viruses, bacteria, cancer cells, or cancer tissues may be loaded as a foreign antigen to the microvesicle.

As an immunopotentiator for increasing an antibody response or a T-cell immune response, double-stranded RNA (dsRNA), cholera toxin, and/or alum may be loaded. Among the immunomodulator loadable with the aim of increasing antigen-specific immune responses are cytokines such as IL-2, IL-4, IL-6, IL-12, IL-17, and IFN-gamma, and growth factors such as VEGF and fibroblast growth factor (FGF)-2.

In addition to the active ingredient selected from among anticancer agents, anti-inflammatory agents, angiogenesis inhibitors, peptides, proteins, toxins, nucleic acids, beads, microparticles, nanoparticles and combinations thereof, the pharmaceutical composition of some embodiments of the present invention may comprise a pharmaceutically acceptable carrier, for example, saline, sterile water, Ringer's solution, buffered saline, cyclodextrin, dextrose solution, maltodextrin solution, glycerol, ethanol, liposome, or a combination thereof. If necessary, the pharmaceutical composition may further comprise a typical additive such as an antioxidant, buffer, etc. In addition, the pharmaceutical composition may be formulated into injections such as aqueous solutions, suspensions, emulsions, etc., pills, capsules, granules or tablets, with the aid of a diluent, a dispersant, a surfactant, a binder and/or a lubricant. Moreover, the pharmaceutical composition may be formulated into suitable dosage forms according to a method well known in the art or the method disclosed in Remington's Pharmaceutical Science, Mack Publishing Company, Easton Pa. No particular limitations are imparted to the formulations of the pharmaceutical composition. Preferably, the pharmaceutical composition may be formulated into injections or inhalable forms.

No particular limitations are imparted to the administration of the pharmaceutical composition of the present invention. The pharmaceutical composition may be administered orally or parenterally such as intravenously, subcutaneously, intraperitoneally, via inhalation, or topically. The amount of the active ingredient in the pharmaceutical composition of at least certain embodiments of the present invention may vary depending on various factors including patient's weight, age, gender and health condition, diet, the time of administration, the route of administration, the rate of excretion, the severity of disease, and the like. The term "daily dose" means an amount of the therapeutically effective ingredient of at least certain embodiments of the present invention which is sufficient to reduce the condition of disease when it is administered to a subject in need thereof. A suitable dose of the active ingredient in the pharmaceutical composition of at least certain embodiments of the present invention may depend on the kind of the loaded compounds, disease severity, and the condition of a subject in need of treatment, and can be determined by those skilled in the art. For example, the suitable dose of the composition of certain embodiments of the present invention may vary depending on the patient's weight, age, gender and health condition, the route of administration, and the severity of disease, and generally ranges from 0.1 to 1000 mg/day, and preferably from 1 to 500 mg/day for an adult patient with a weight of 70 kg. The total effective amount of the pharmaceutical composition of at least certain embodiments of the present invention can be administered to patients in a single dose or can be administered by a fractionated treatment protocol, in which multiple doses are administered over a more prolonged period of time.

As used herein, the term "subject" refers to an animal in need of the treatment of cancer, vascular diseases or inflammatory diseases, including a human, or non-human mammals such as primates, mice, rats, dogs, cats, horses, cows, etc.

Contemplated by the present invention in accordance with a still further aspect is a composition for the delivery of a therapeutic, a diagnostic, and/or a vaccine substance, comprising the protoplast-derived microvesicles of at least some embodiments of the present invention.

Also contemplated by the present invention in accordance with still another aspect is a system for the delivery of a therapeutic, a diagnostic, and/or a vaccine substance, comprising the protoplast-derived microvesicles of at least some embodiments of the present invention.

The therapeutic, diagnostic, and/or vaccine substance is as illustrated above.

In accordance with yet another aspect thereof, the present invention addresses a method for the preparation of protoplast-derived microvesicles loaded with a therapeutic, a diagnostic, or a vaccine substance.

The microvesicles may be a microvesicle that has spontaneously been shed from a cell, or may be an artificially synthesized microvesicle.

The protoplast-derived microvesicles according to some embodiments of the present invention may be constructed using various mechanical, electrical or chemical methods. Examples of the methods include cytolysis using osmosis, electroporation, sonication, homogenization, detergent treatment, freeze-thawing, extrusion, mechanical degradation, and chemical treatment, but are not limited thereto. In a mechanical degradation method, a solution of cells is shaken together with metal, ceramic or sufficiently hard plastic balls. In the context of extrusion, cells are forced to sequentially pass through filters starting with large pores and going down to smaller pores. For example, cells are sequentially passed through three filters with respective pore sizes of 10 µm→5 µm→1 µm to form microvesicles.

In one embodiment thereof, the preparation method according to the present invention comprises the following steps: removing a cell wall from cells to give protoplasts; constructing microvesicles in a suspension of the protoplasts; and isolating the microvesicles from the suspension.

In another embodiment thereof, the preparation method according to the present invention comprises the following steps: externally loading a therapeutic, a diagnostic, or a vaccine substance to cells and removing a cell wall from the cells to give protoplasts; constructing microvesicles from a suspension of the protoplasts; and isolating the microvesicles from the suspension.

In another embodiment thereof, the preparation method according to the present invention comprises the following steps: removing a cell wall from cells to give protoplasts; externally loading a therapeutic, diagnostic, or vaccine substance to the protoplasts; constructing microvesicles in a suspension of the substance-loaded protoplasts; and isolating the microvesicles from the suspension.

In another embodiment thereof, the preparation method according to the present invention comprises the following steps: removing a cell wall from cells to give protoplasts; constructing microvesicles in a suspension of the protoplasts in the presence of a therapeutic, diagnostic, or vaccine substance; and isolating the microvesicles from the suspension.

In another embodiment thereof, the preparation method according to the present invention comprises the following steps: removing a cell wall from cells to give protoplasts; constructing microvesicles from a suspension of the protoplasts; adding a therapeutic, diagnostic, or vaccine substance to a suspension of the microvesicles to load the substance to the microvesicles; and isolating the microvesicles loaded with the therapeutic, diagnostic, or vaccine substance from the suspension.

In another embodiment thereof, the preparation method according to the present invention comprises the following steps: removing a cell wall from cells to give protoplasts; constructing microvesicles in a suspension of the protoplasts; isolating the microvesicles from the suspension; and adding a therapeutic, diagnostic, or vaccine substance to a suspension of the isolated microvesicles to load the substance to the microvesicles.

The method may further comprise isolating the microvesicles loaded with a therapeutic, diagnostic or vaccine substance from the suspension of microvesicles.

The isolation may be carried out using a process selected from the group consisting of ultracentrifugation, density gradient, filtration, dialysis, and free flow electrophoresis.

A density gradient process, one of the most popular processes for distinguishing materials with different densities, can be applied to the isolation of the microvesicles of some embodiments of the present invention because their densities are different from those of free molecules. For use in the density gradient process, a medium may be selected from among, but not limited to, Ficoll, glycerol, sucrose and OptiPrep™. Microvesicles loaded with or without therapeutic or diagnostic substances may be separated from each other when taking advantage of differences in density therebetween. A density gradient process may be used in combination with centrifugation or electrophoresis. Microvesicles can also be isolated by gel filtration or ultrafiltration. Instead of filtration, dialysis may be adopted to remove small molecules. In addition, free flow electrophoresis is useful for isolating microvesicles of certain embodiments of the present invention.

According to purpose, microvesicles within a certain size range may be selected before use. The selection of microvesicles within a certain size range may be carried out before, during or after loading therapeutic or diagnostic substances thereinto.

The therapeutic, diagnostic, and/or vaccine substance loaded to the protoplast-derived microvesicles are as defined above, and no particular limitations are imposed thereon.

For example, the substance to be loaded to the protoplast-derived microvesicles may come from the cells serving as a source of the protoplast-derived microvesicles, or may be foreign to the cells. The substance may be a single material or a combination of two or more different materials. Loading a therapeutic, a diagnostic, and/or a vaccine substance to the protoplast-derived microvesicles means displaying the substance on the surface of the protoplast-derived microvesicles or encapsulating the substance within the microvesicles, but the present invention is not limited thereby.

In another embodiment of the present invention, the preparation method may further comprise modifying a part of membrane components. There are various processes for modifying cell membrane components. For example, when microvesicles are constructed from a mixture of a fusion protein and cells, the fusion protein may be displayed on the microvesicles. Microvesicles may be converted into stealth-microvesicles by coating with polyethylene glycol. The addition of cyclodextrin to microvesicles may reduce the non-specific targeting of the microvesicles. Exhibiting both hydrophilicity and hydrophobicity, cyclodextrin, when attached onto the surface of microvesicles, can act to block non-specific binding between lipids. The microvesicles may be chemically modified. For example, after microvesicles are constructed from cells whose membrane or transmembrane proteins are exposed to the outside, various molecules may be chemically bound to the thiol group of cystein residues on the exposed region of the protein. Chemical modifications can also be achieved by binding various molecules to amine groups on membrane proteins.

According to another embodiment of the present invention, the preparation method may further comprise removing microvesicles whose membranes are topologically different from those of the protoplasts of origin. After construction of microvesicles, only those microvesicles that have the same membrane topology as that of the source cells may be selected according to purposes. Using antibodies recognizing cytoplasmic domains of membrane proteins, microvesicles in which the cytoplasmic domains are exposed to the outside can be removed. That is, the microvesicles in which the plasma membrane is turned inside out are removed, and only the microvesicles in which the extracellular domains of membrane proteins are positioned so as to be directed towards the outside remain.

In accordance with a yet further aspect thereof, the present invention addresses a method for delivering a therapeutic, a diagnostic, and/or a vaccine substance to a specific cell or tissue, comprising the use of protoplast-derived microvesicles loaded with the substance.

In detail, the method for delivering a therapeutic, a diagnostic, and/or a vaccine substance to a specific cells or tissue comprises using microvesicles which have a membrane derived from a protoplast, are smaller in size than the protoplast, and are loaded with the substance. If necessary, protoplast-derived microvesicles loaded with targeting molecules and/or fusogens may be used to deliver the therapeutic, the diagnostic, and/or the vaccine substance to a specific cell or tissue.

No limitations are imposed on the specific cell or tissue. For example, the specific cell may be an endothelial cell, a cancer cell, an inflammatory cell, or an immune cell. The specific tissue may include vessels, cancer tissues, and inflammatory tissues. In addition, the therapeutic, the diagnostic, or the vaccine substance is as illustrated above.

In one embodiment of the present invention, two or more different substances may be delivered to specific cells or tissues.

In another embodiment of the present invention, two or more different microvesicles selected from the group consisting of a microvesicle loaded with one substance, a microvesicle loaded with two or more substances, and a combination thereof may be used to deliver the substance(s). For example, two or more different microvesicles may be administered simultaneously.

In another embodiment of the present invention, two or more different microvesicles selected from the group consisting of a microvesicle loaded with one substance, a microvesicle loaded with two or more substances, and a combination thereof may be administered sequentially.

In detail, microvesicles with two or more different substances simultaneously loaded thereto may be used to deliver the substances. Alternatively, microvesicles loaded with different substances individually or in combination are employed in combination so that two or more different substances can be delivered. In order to deliver three different substances, for instance, a first, a second and a third microvesicle may be loaded with the three different substances, respectively. On the other hand, a fourth microvesicle with two different substances simultaneously loaded thereto and a fifth microvesicle with another different substance loaded thereto may be used to deliver the three different substances. The first, the second and the third microvesicles may be used simultaneously or sequentially. Likewise, the fourth and the fifth microvesicles may be used simultaneously or sequentially.

If necessary, a nuclease may be employed during the construction of the protoplast-derived microvesicles to remove nucleic acids unnecessary for the delivery of a therapeutic, diagnostic, and/or vaccine substance from the microvesicles.

In accordance with an additional aspect thereof, the present invention envisages a method for the therapy and/or diagnosis of a disease, comprising using protoplast-derived microvesicles loaded with a diagnostic or therapeutic substance to deliver the substance to specific cells or tissues. That is, the microvesicle may be used to deliver a diagnostic or therapeutic substance to target cells, tissues, or blood.

From cell protoplasts, microvesicles can be readily constructed in various sizes like liposomes, and loaded with various therapeutic, diagnostic, or vaccine substances to be delivered. Hence, microvesicles may be used for sole or combined therapy or diagnosis or both of therapy and diagnosis (theragnosis, pharmacodiagnosis). In this context, the substances to be delivered may be present inside the microvesicles when encapsulated, on the surface of the microvesicles when binding to a receptor, or within the lipid bilayer when buried or embedded therein like a transmembrane protein.

Thanks to the EPR (Enhanced Permeability and Retention) effect, generally, molecules with a size of 100 nm or greater may accumulate in cancer tissue for a longer period of time than they do in normal tissues. Accordingly, a drug loaded to microvesicles with a size of 100 nm or greater is advantageous in diagnosis and therapy because it can stay much longer in cancer tissue, thereby enhancing a therapeutic or diagnostic effect. On the other hand, when inhaled, only particles with a size of 1 µm or smaller are allowed to reach the alveoli due to the pulmonary structure. A substance, for example, an inflammation inhibitor for the treatment of asthma, can be delivered to lung tissue if it is loaded to microvesicles which are smaller than 1 µm in size. As described, various sizes of microvesicles may be constructed depending on the tissue to which the loaded substance is to be applied. Preferably, the microvesicles of certain embodiments of the present invention range in size from 10 nm to 10 µm.

Also contemplated by the present invention in accordance with another additional aspect is a method for the prophylaxis and/or therapy of a disease, comprising using protoplast-derived microvesicles loaded with a vaccine substance to deliver the vaccine substance to a specific cell or tissue. The vaccine substance is as described above.

In accordance with a further additional aspect thereof, the present invention addresses a kit for the diagnosis of a disease, comprising a protoplast-derived, sub-protoplast size microvesicle loaded with a primer, a probe, an antisense nucleic acid or an antibody as an active ingredient necessary for the diagnosis.

The protoplast-derived microvesicles with therapeutic and/or diagnostic substances loaded thereto and the preparation method thereof in accordance with certain embodiments of the present invention may be applied to the delivery of the substances to target cells or tissues in vitro and/or in vivo. For instance, protoplast-derived microvesicles with an enzyme, a therapeutic, a diagnostic, or a vaccine substance loaded thereto, and a preparation method thereof may be used for in vitro experiments. Further, based on the data obtained through in vitro experiments, the microvesicles and the preparation method thereof can be applied in vivo so as to change diseased cells into curable ones, but the present invention is not limited thereby.

A better understanding of at least certain embodiments of the present invention may be obtained through the following examples which are set forth to illustrate, but are not to be construed as limiting, the present invention.

EXAMPLES

Example 1

Preparation of Protoplast from Gram-Negative Bacteria by Treatment with Lysozyme With reference to FIG. 1, there is a schematic view illustrating the preparation of protoplasts from Gran-negative bacteria by lysozyme hydrolysis, and the derivation of microvesicles from the protoplasts, with the concomitant loading of a drug to the protoplasts or microvesicles in each step.

According to FIG. 1, protoplasts were prepared from Gram-negative bacteria. In this regard, the Gram-negative bacterium *E. coli* w3110 msbB was grown to $O.D._{600}=1.0$ in LB broth, and spun down at 3,000×g for 10 min. The cell pellet thus obtained was resuspended in 10 mL of a protoplasting buffer to which EDTA was then slowly added to a final concentration of 0.01 M, followed by incubation for 40 min at 37° C., with shaking at 100 rpm. After centrifugation at 3,000×g for 10 min, the cell pellet thus obtained was resuspended in 100 mL of protoplasting buffer containing 0.02 M $MgCl_2$.

The suspension was incubated for 2 hrs at 37° C. in the presence of 2 mg/mL lysozyme, with shaking at 100 rpm, and spun down at 5,000×g for 10 min to afford protoplasts as a pellet while the supernatant contained the outer membrane and cell wall. The protoplast pellet was suspended in 3 mL of TBS (Tris buffered saline) containing $CaCl_2$ and $MgCl_2$ at a concentration of 0.02 M.

In order to confirm the preparation of protoplasts, bacterial cells were labeled with biotin, and protoplasts were prepared from the biotin-labeled bacterial cells. After centrifugation at 5,000×g for 10 min, intact cells were separated from the protein-containing supernatant. The protein-containing supernatants from the samples, and the supernatant containing the outer membrane and cell wall removed upon the preparation of protoplasts, were individually mixed with a 5× loading dye (250 mM Tris-HCl, 10% SDS, 0.5% bromophenol blue, 50% glycerol), in such an amount that the concentration of the loading dye was diluted to 1×. The mixtures were boiled at 100° C. for 5 min, and loaded into an 8% polyacrylamide gel. After electrophoresis at 80 V for 2 hrs, the proteins were transferred onto a PVDF (polyvinylidene fluoride) membrane at 400 mA for 2 hrs. The membrane was blocked for 2 hrs in a 3% solution of skim milk in PBS, incubated at 4° C. for 12 hrs with a peroxidase-conjugated anti-biotin antibody, and washed for 30 min with PBS, followed by visualization with an ECL substrate (enhanced chemiluminescence, Amersham Co. No. RPN2106). The result is shown in FIG. 2.

Figure 2:
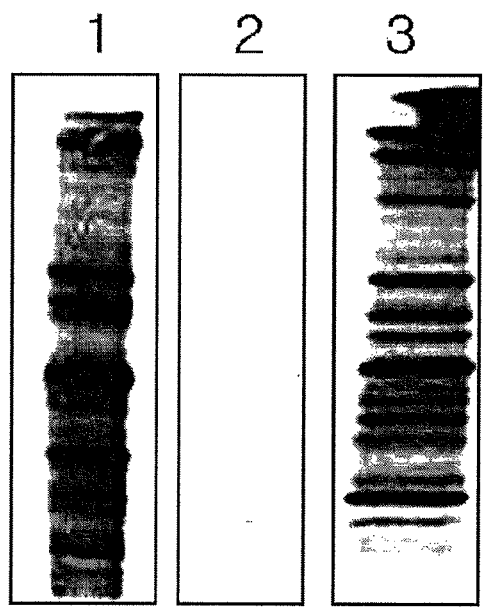
FIG. 2 illustrates the accurate construction of protoplasts from bacterial cells.

As can be seen in FIG. 2, an antibody reaction to biotin was detected in the bacteria, but not in the protoplasts. Also, the antibody reaction to biotin was observed in the supernatant containing the biotinylated outer membrane and cell wall, indicating that the outer membrane and the cell wall were removed from the bacteria by treatment with lysozyme. From the result, it was accordingly apparent that protoplasts free of outer membranes and cell walls were prepared by lysozyme hydrolysis.

Example 2

Construction of Microvesicles Derived from Protoplasts of Gram-Negative Bacteria by Extrusion According to the procedure illustrated in the scheme of FIG. 1, protoplast-derived microvesicles were prepared. From among those suggested in FIG. 1, extrusion and a density gradient were selected.

The protoplasts of Gram negative bacteria prepared in Example 1 were passed three times through each of membrane filters with a pore size of 10 μm, 5 μm, and 1 μm, in that order. In a 5 mL ultracentrifuge tube were sequentially placed 1 mL of 50% OptiPrep, 1 mL of 5% OptiPrep, and 3 mL of the cell suspension effluent from the membrane filters. Ultracentrifugation at 100,000×g for 2 hours formed a layer of microvesicles between 50% OptiPrep and 5% OptiPrep.

Example 3

Properties of Microvesicles Derived from Protoplasts of Gram-Negative and Gram-Positive Bacteria Microvesicles were constructed from protoplasts of the Gram-negative bacterium *E. coli* and the Gram-positive bacterium *Bacillus subtilis* according to the methods of Examples 1 and 2.

Each of the microvesicles was adsorbed for 3 min to a glow-discharged carbon-coated copper grid. The grid was washed with distilled water, and stained with 2% uranylacetate before observation under a JEM101 electron microscope (Jeol, Japan). The electron microscope images are shown in FIGS. 3 and 4.

Figure 3:
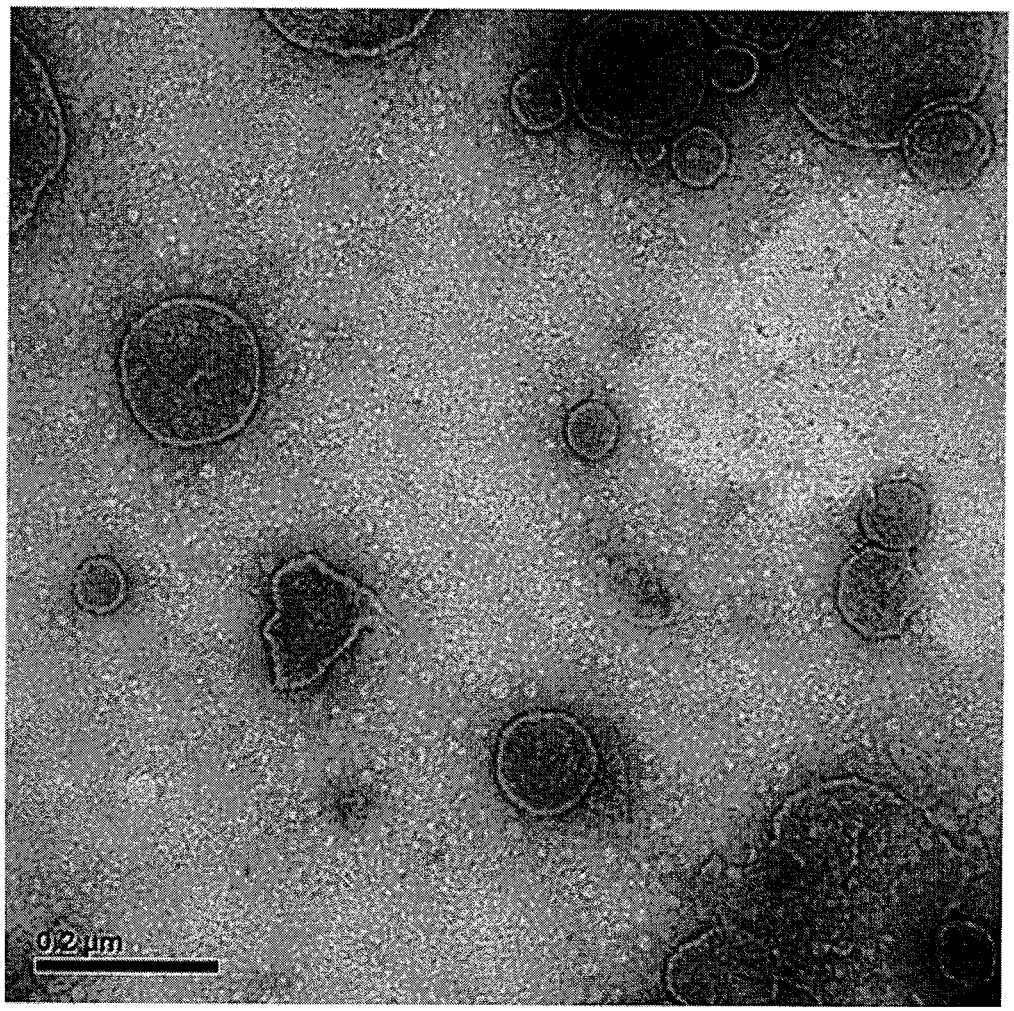
FIG. 3 is a TEM image showing microvesicles derived from Gram-negative protoplasts.
Figure 4:
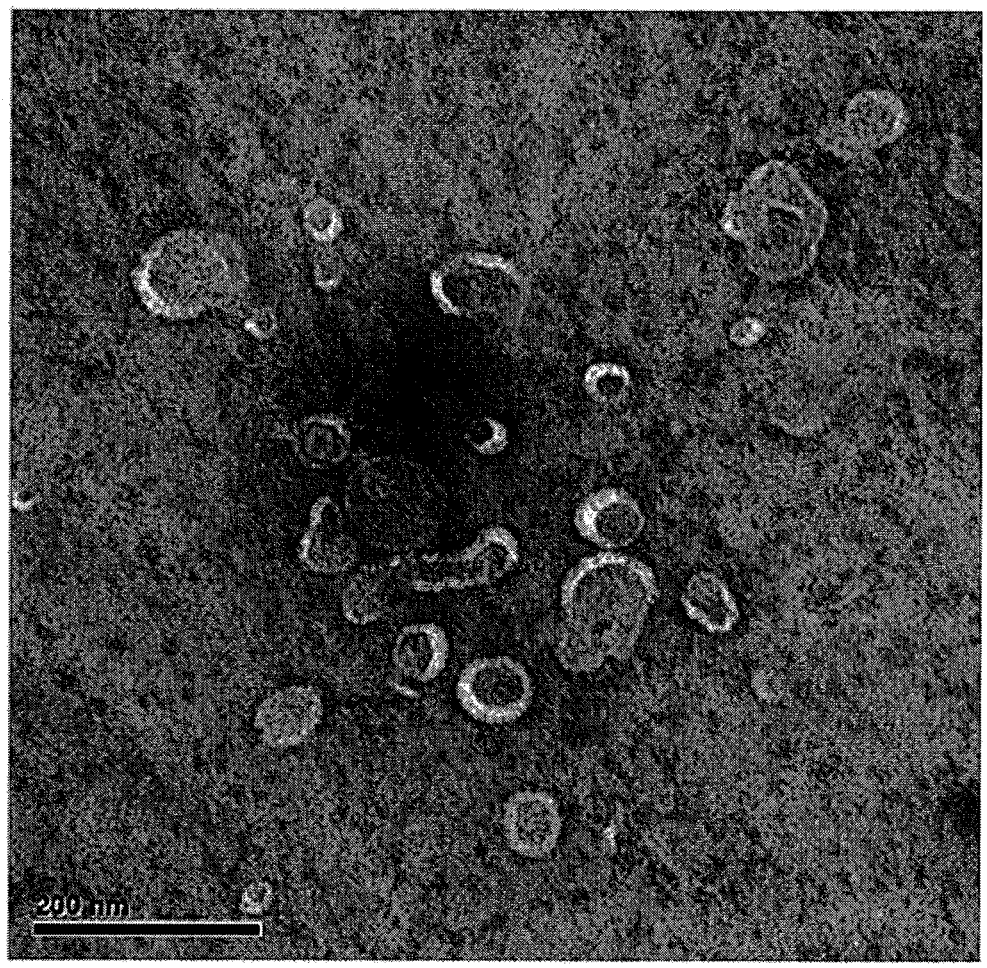
FIG. 4 is a TEM image showing microvesicles derived from Gram-positive protoplasts.

FIGS. 3 and 4 are TEM (transmission electron microscope) images of the microvesicles derived from protoplasts of the Gram-negative bacterium *E. coli* and the Gram-positive bacterium *B. subtilis*, respectively. As can be seen in the TEM images of FIGS. 3 and 4, the microvesicles constructed from the protoplasts of bacterial cells by extrusion consisted of a lipid bilayer, and were generally spherical with a size of 100~200 nm for those derived from Gram-negative bacteria and a size of 50~100 nm for those derived from Gram-positive bacteria.

Each of the microvesicles was diluted to a concentration of 5 μg/ml in 1 mL of PBS which was then placed in a cuvette, and analyzed for particle sizes using a dynamic light scattering (DLS) particle size analyzer. The results are given in FIGS. 5 and 6.

Figure 5:
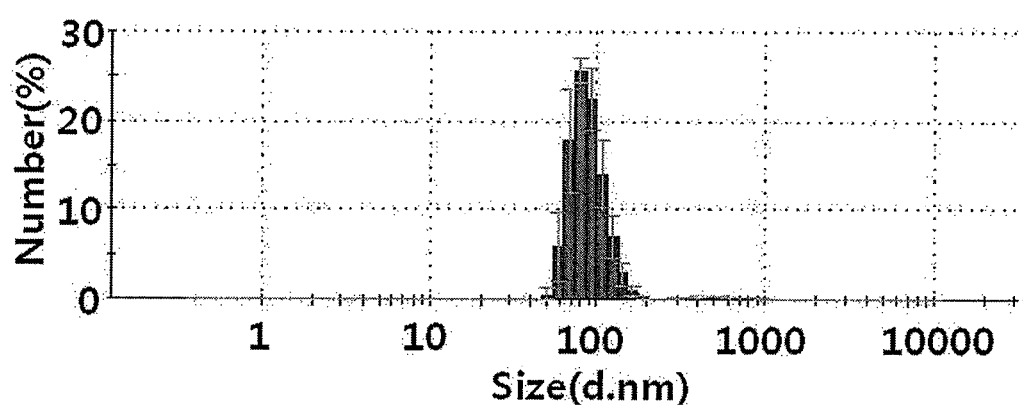
FIG. 5 is a graph showing particle sizes of microvesicles derived from Gram-negative protoplasts.
Figure 6:
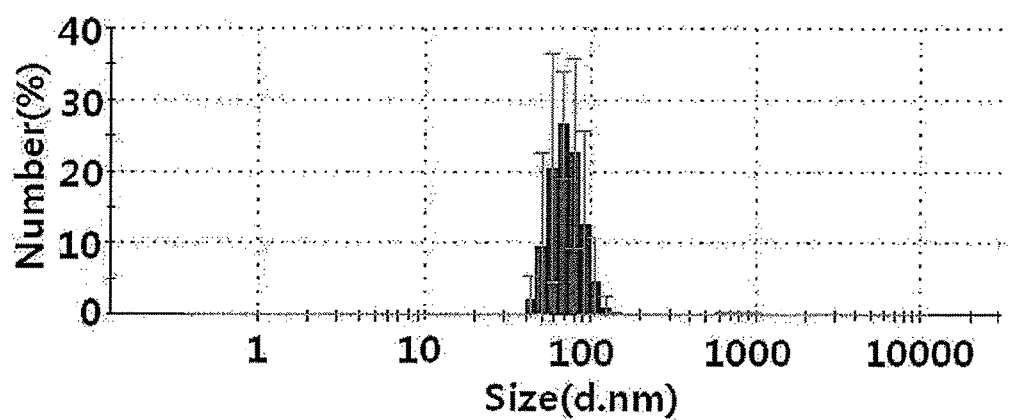
FIG. 6 is a graph showing particle sizes of microvesicles derived from Gram-positive protoplasts.

FIGS. 5 and 6 are graphs showing size distributions of the microvesicles constructed from the protoplasts of the Gram-negative bacterium *E. coli* and the Gram-positive bacterium *B. subtilis*, respectively. As can be seen in FIGS. 5 and 6, the microvesicles derived from protoplasts of Gram-negative and Gram-positive bacteria ranged in size from 100 to 200 nm, and from 50 to 100 nm, respectively.

Example 4

In Vitro Comparison of Side Effects Between Bacterial Cell- and Bacterial Protoplast-Derived Microvesicles Microvesicles derived from protoplasts of the Gram-negative bacterium *E. coli* and the Gram-positive bacterium *S. aureus* were prepared using the methods described in Examples 1 and 2. Separately, conventional methods were used to prepare Gram-negative bacterium-derived microvesicles [Proteomics. 2007 September; 7(17): 3143-53] and Gram-positive bacterium-derived microvesicles [Proteomics. 2009 December; 9(24): 5425-36].

An examination was made to see whether these microvesicles provoke immune responses. For this, macrophages were treated with the bacterial cell- and bacterial protoplast-derived microvesicles, and the pro-inflammatory cytokine TNF-α secreted by macrophages were quantitatively analyzed using ELISA.

Each microvesicle was applied at a concentration of 1,000 ng/mL for 16 hrs to mouse macrophages (Raw 264.7) to induce an immune response. After treatment for 16 hrs, the conditioned media were obtained, and centrifuged at 500×g for 5 min to give supernatants. Separately, 96-well plates coated with an anti-TNF-α antibody were blocked with 100 µl of 1% BSA/PBS per well for 1 hr. The supernatants of the conditioned media were diluted 1/10, and the dilutions were plated into the plates and incubated at room temperature for 2 hours. After incubation with a biotin-conjugated, detection antibody to TNF-α for 2 hours, the plates were washed with 0.05% Tween-20 in PBS. Treatment with streptavdin-POD for 20 min was followed by color development with a BM-POD substrate.

Figure 7:
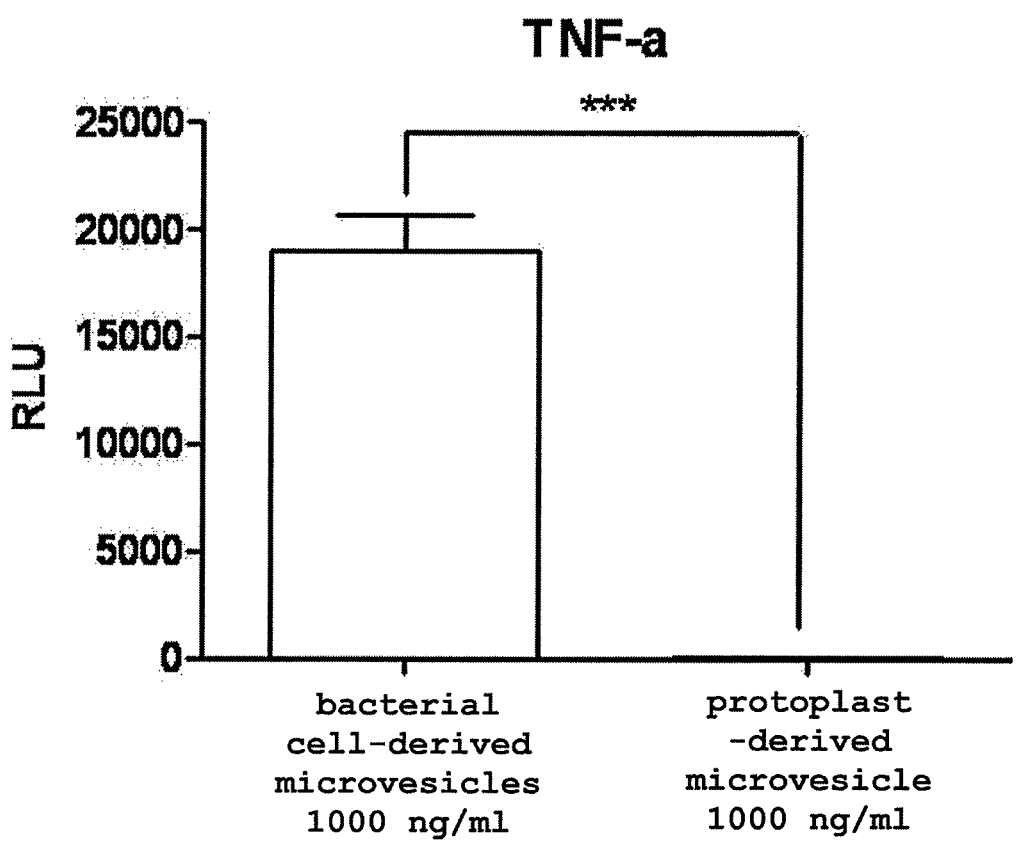
FIG. 7 is a graph showing that the Gram-negative protoplast-derived microvesicles cause no side effects.
Figure 8:
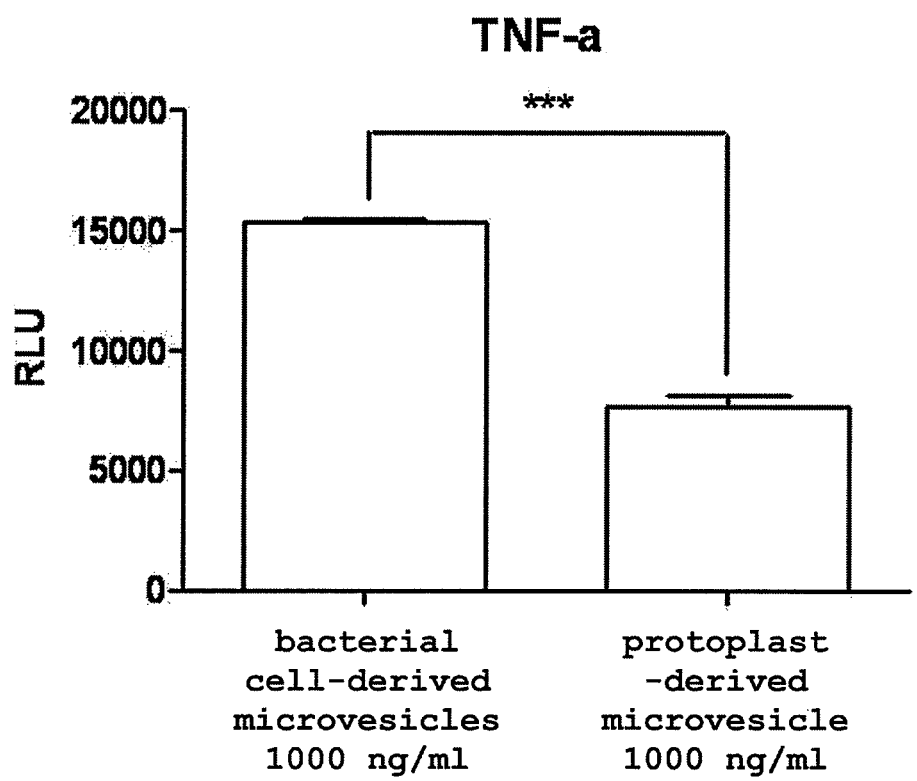
FIG. 8 is a graph showing that the Gram-positive protoplast-derived microvesicles cause no side effects.

FIG. 7 is a graph showing levels of TNF-α secreted by macrophages in the presence of Gram-negative bacterial cell-derived or Gram-positive bacteria protoplast-derived microvesicles. FIG. 8 shows levels of TNF-α secreted by macrophages treated with Gram-positive bacterial cell- or Gram-positive bacterial protoplast-derived microvesicles.

As is understood from the data of FIG. 7, the Gram-negative bacterial cell-derived microvesicles containing both the outer membrane and the cell wall provoked immune responses to increase the secretion of TNF-α, whereas the Gram-negative bacterial protoplast-derived microvesicles free of the outer membrane and the cell wall did not induce the secretion of TNF-α, like the control.

In addition, as shown in FIG. 8, the microvesicles derived from cells of the Gram-positive bacterium *B. subtilis* induced macrophages to secrete TNF-α at an increased level while a lower level of TNF-α was secreted in the presence of the microvesicles derived from the cell wall-free protoplasts.

These data imply that bacterial protoplast-derived microvesicles evoke an inflammatory response at a significantly lower level, with a minimum side effect, compared to the bacterial cell-derived microvesicles.

Example 5

In Vivo Comparison of Side Effects Between Bacterial Cell- and Bacterial Protoplast-Derived Microvesicles Microvesicles derived from protoplasts of the Gram-negative bacterium *E. coli* were prepared using the methods described in Examples 1 and 2. Gram-negative bacterial cell-derived microvesicles were also prepared.

Mice were intraperitoneally injected with 25 µg of the bacterial cell-derived microvesicles, or 500 µg of the bacterial protoplast-derived microvesicles, and examined for survival with time. The results are shown in FIG. 9.

Figure 9:
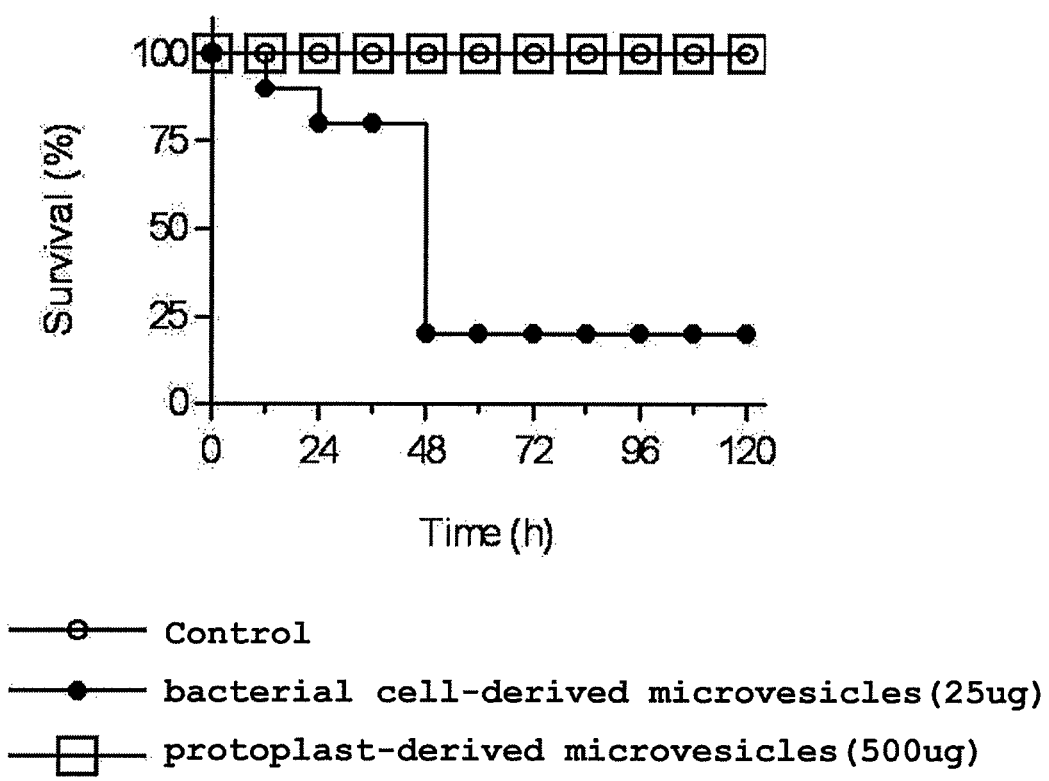
FIG. 9 is a graph showing that the Gram-negative protoplast-derived microvesicles do not cause side effects in mice.

Of ten mice, as can be seen in FIG. 9, eight died 48 hrs after injection with the bacterial cell-derived microvesicles, whereas none were dead even after the bacterial protoplast-derived microvesicles were injected at a 20-fold higher dose.

Six hours after the intraperitoneal injection of 5 µg of the bacterial cell-derived or bacterial protoplast-derived microvesicles into mice, blood samples were obtained from the mice and used to examine whether the mice were induced to express the inflammatory cytokine IL-6. In this regard, the blood samples were stored at room temperature for 30 min, and then at 4° C. for 1 hr to separate serum. Blood cells were spun down at 1,300×g for 20 min. Separately, 96-well plates coated with an anti-IL-6 antibody were blocked with 100 µl of 1% BSA/PBS per well for 1 hr. The supernatants were diluted 1/4, and the dilutions were plated into the plates and incubated at room temperature for 2 hours. After incubation with a biotin-conjugated detection antibody to IL-6 for 2 hours, the plates were washed with 0.05% Tween-20 in PBS. Treatment with streptavdin-POD for 20 min was followed by color development with a BM-POD substrate. The result is depicted in FIG. 10.

Figure 10:
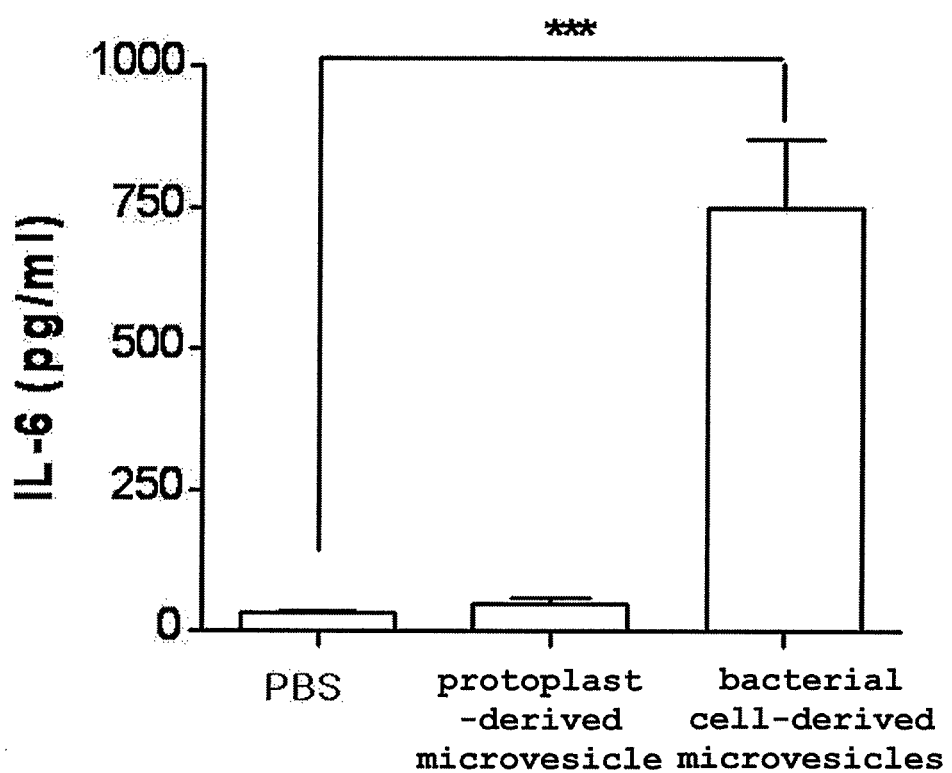
FIG. 10 is a graph showing that the Gram-positive protoplast-derived microvesicles do not induce the production of IL-6 in mice

As is understood from the data of FIG. 10, the level of the pro-inflammatory cytokine IL-6 in blood was increased six hrs after injection of the bacterial cell-derived microvesicles, whereas no changes were detected in the group administered with the bacterial protoplast-derived microvesicles.

The data obtained above indicates that when injected, bacterial cell-derived microvesicles induce systemic inflammation, whereas no side effects are caused even by a high concentration of bacterial protoplast-derived microvesicles.

Example 6

Preparation of Microvesicles Loaded with Bacterial Plasmid

DH5α, whether transformed with the recombinant vector pMSCV-EGFP or not, was cultured and used to prepare protoplast-derived microvesicles in the same manner as in Examples 1 and 2. PCR (polymerase chain reaction) was performed using EGFP primers with the microvesicles serving as a template. The DNA thus amplified was confirmed on agarose gel (TBE buffer, 1%) by electrophoresis, and the result is given in FIG. 11. The EGFP primers were as follows.

```
Forward primer:
                                        (SEQ ID NO. 1)
5'-GGAATTCCATATGGTGAGCAAGGGCGAGGA-3'

Reverse primer:
                                        (SEQ ID NO. 2)
5'-ACGCGTCGACTTACTTGTACACCTCGTCCAT-3'
```

Figure 11:
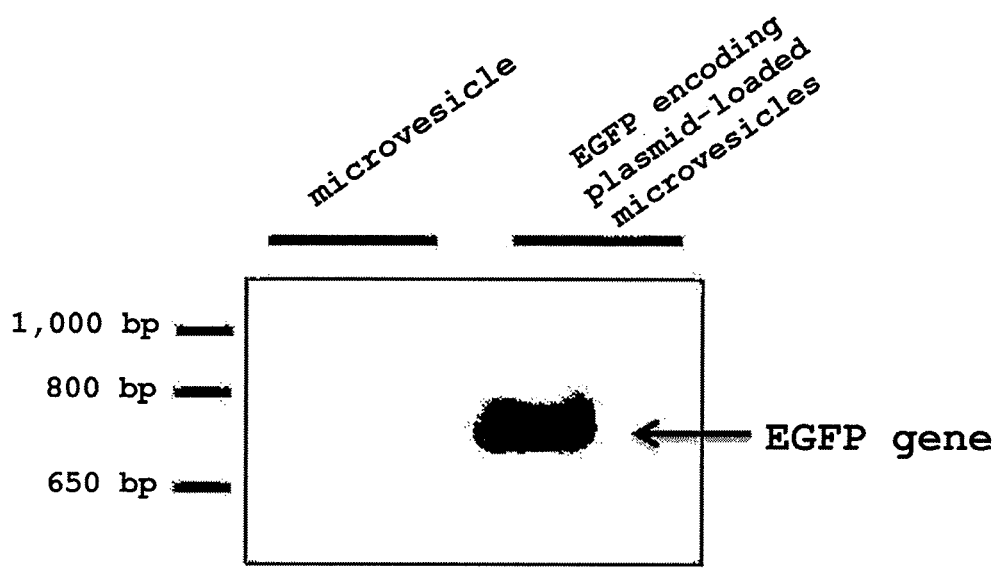
FIG. 11 is a view showing the capacity of the protoplast-derived microvesicles to load a plasmid thereto.

As can be seen in FIG. 11, the microvesicles loaded with the plasmid carrying an EGFP gene were observed on the agarose gel in terms of the gene amplified with the EGFP primers, while no observations were detected in the lane of the microvesicles void of the EGFP gene.

In order to examine the integrity of the plasmid loaded to the microvesicles, the plasmid was extracted from the microvesicles using a Geneall miniprep kit (GENE=cat. #101-102). The extracted plasmid was transformed into *E. coli* BL21 by heat shock. This *E. coli* strain was incubated at 37° C. for 1 hr in 1 mL of LB, and grown at 37° C. for 16 hrs on LB agar plates containing ampicillin. After the appearance of colonies on the plates, one was grown at 37° C. to $O.D_{600}=1.0$ in an LB medium containing ampicillin before the plasmid was extracted using a Geneall miniprep kit. The extracted plasmid was treated with restriction enzymes to separate the EGFP gene from the pMSCV vector, and run on an agarose gel (TBE buffer, 1%) by electrophoresis. The enzyme mapping result is given in FIG. 12.

Figure 12:
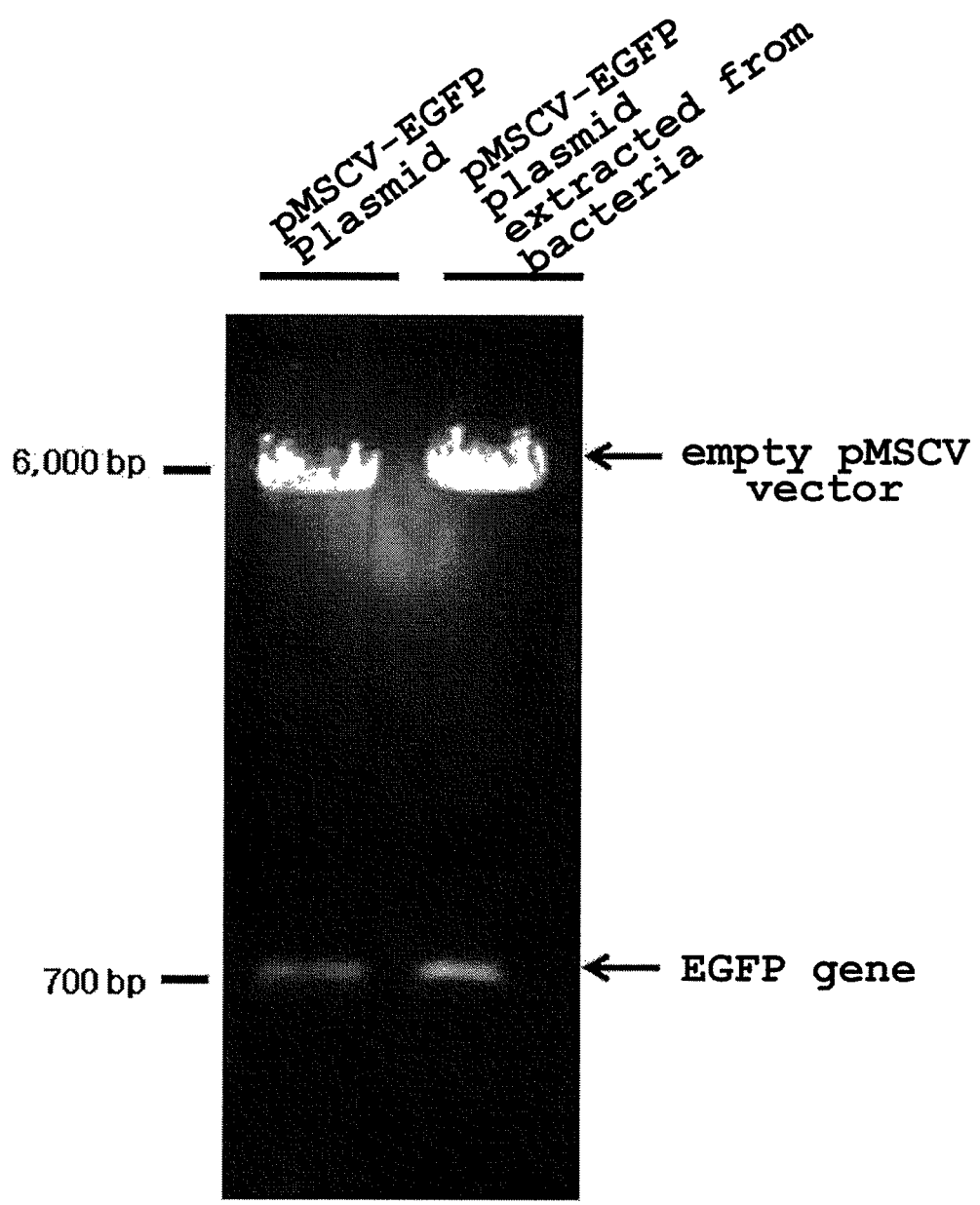
FIG. 12 is a view showing the integrity of a plasmid loaded to the protoplast-derived microvesicles.

As can be seen in FIG. 12, the pMSCV plasmid extracted from the microvesicle carried the EGFP gene, like the recombinant vector pMSCV-EGFP.

From this result, it is apparent that a bacterial plasmid can be loaded to the microvesicles without losing its integrity.

Example 7

Preparation of Microvesicles Loaded with Bacterial Plasmid and Capacity for Delivering the Plasmid to Bacteria The bacterial protoplast-derived microvesicles were examined for their capacity to transform bacteria by delivering a plasmid to the bacteria. First, an EGFP expressing plasmid for use in establishing green fluorescent bacteria was constructed. For this, primers with restriction enzyme sites were designed on the basis of the DNA sequence of EGFP.

```
Forward primer:
                                    (SEQ ID NO. 3)
5'-GGAATTCCATATGGGTGAGCAAGGGC GAGGA-3'

Reverse primer:
                                    (SEQ ID NO. 4)
5'-AGGCGTCGACTTACTTGTACAGCTCG TCCAT-3'
```

(Restriction Enzyme Sites NdeI and SalI are Indicated by Bold Letters)

PCR was performed on genomic DNA carrying a GFP gene in the presence of the primers, and the PCR product thus obtained was purified from the PCR band using a Quiaquick gel purification kit (QIAGEN, cat. #28104). The purified product was digested at 37° C. for 8 hrs with the restriction enzymes NdeI and SalI, and purified again with a Quiaquick PCR purification kit before ligation to the pHCE vector digested with the same enzymes. The resulting recombinant vector was named "pHCE-GFP."

*E. coli* DH5α was transformed with the recombinant vector pHCE-GFP by heat shock, and incubated at 37° C. for 1 hr in 1 mL of LB broth, and grown at 37° C. for 16 hrs on an LB agar plate containing ampicillin. The transformation was confirmed by colony-PCR and enzyme mapping.

Microvesicles loaded with or without pHCE-GFP were constructed from the Gram-negative bacterium *E. coli* with or without the recombinant vector pHCE-GFP, respectively, using the methods disclosed in Examples 1 and 2.

Bacteria transformed with a pHCE vector can be grown on an agar plate because the vector carries an ampicillin-resistant gene. Of course, the bacteria transformed with pHCE-GFP appears green fluorescent because of the presence of an EGFP gene in the plasmid.

*E. coli* DH5α was grown at 37° C. for 16 hrs on a typical LB plate, and layered with 10 μg of the pHCE-GFP plasmid-loaded microvesicles. Then, the cells were streaked over agar plates containing ampicillin according to time, followed by examining the expression of green fluorescence.

Figure 13:
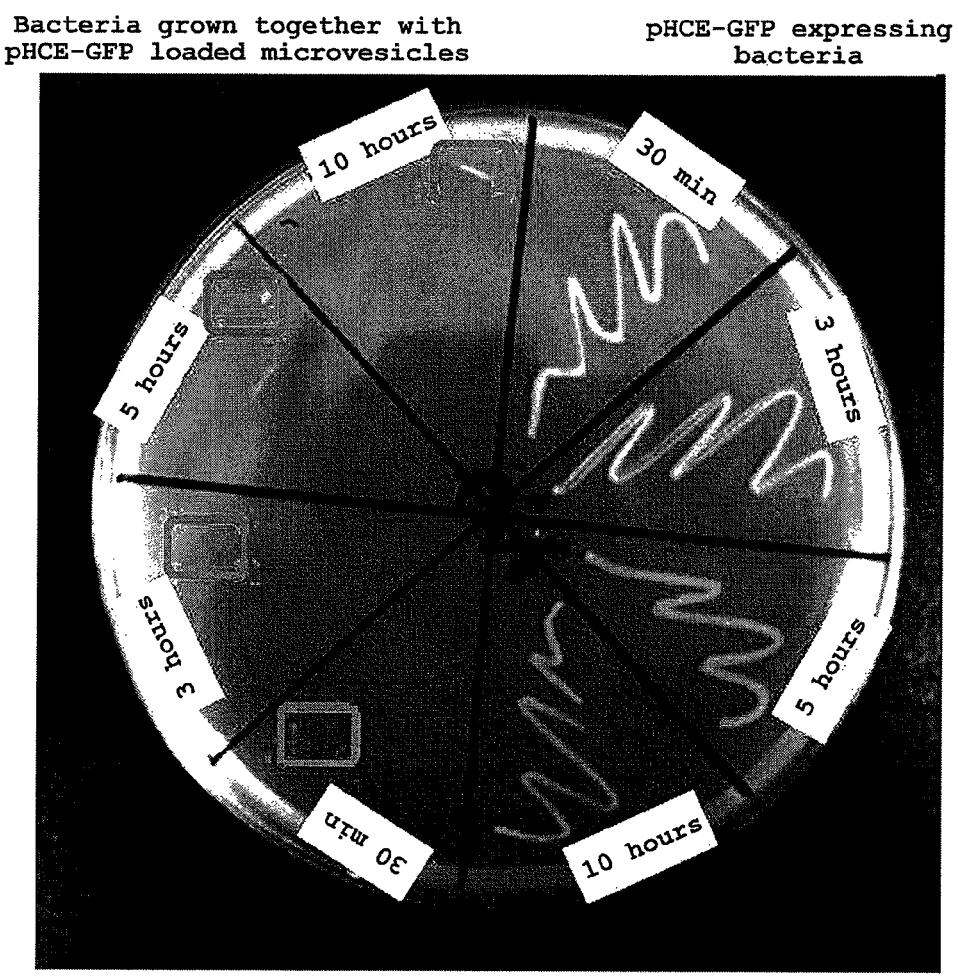
FIG. 13 is a view showing the protoplast-derived microvesicle-mediated delivery of a plasmid to bacteria.

As shown in FIG. 13, microvesicles loaded with the pHCE-GFP plasmid delivered the plasmid to the cells to accomplish the transformation.

The data implies that bacterial protoplast-derived microvesicles can be loaded with a plasmid and deliver it to bacteria.

Example 8

Delivery Capacity and Immune Response Induction of Bacterial Antigen Protein-Loaded Microvesicles The following experiments were carried out to examine whether bacterial protoplast-derived microvesicles can be used as an antigen carrier to induce antibody formation. For this, EGFP, which cannot induce antibody formation by itself, was employed for testing whether microvesicles can induce EGFP antibody formation.

From the Gram-negative bacterium *E. coli*, whether transformed with the recombinant vector pHCE-GFP as in Example 7 or not, microvesicles loaded with or without pHCE-GFP were constructed, respectively, using the methods disclosed in Examples 1 and 2.

An examination was made of the ability of the microvesicles to induce antibody formation and cause an immune response. Mice were intraperitoneally injected three times at regular intervals of seven days with PBS, 5 μg of microvesicles, 5 μg of EGFP-loaded microvesicles, or 2.5 μg of EGFP corresponding to 5 μg of EGFP-loaded microvesicles, respectively. Each group consisted of five mice. Seven days after the final injection, blood samples were taken from the eyes of the mice, incubated at room temperature for 30 min, stored at 4° C. for 1 hr, and centrifuged at 1,300×g for 20 min. The supernatants free of cells were taken.

The formation of an EGFP-specific antibody in the mice was confirmed as follows. Each well of 96-well plates was coated with 100 ng of an EGFP protein, and blocked for 1 hr with 100 μl of 3% BSA/PBS. The supernatants from the mouse blood were diluted 1/1000, added to each well, and incubated at room temperature for 2 hrs, followed by incubation with an HRP-conjugated anti-mouse IgG antibody or anti-mouse IgE for 1 hr. After washing with 0.05% Tween-20 in PBS, a color was developed with a BM-POD substrate.

Figure 14:
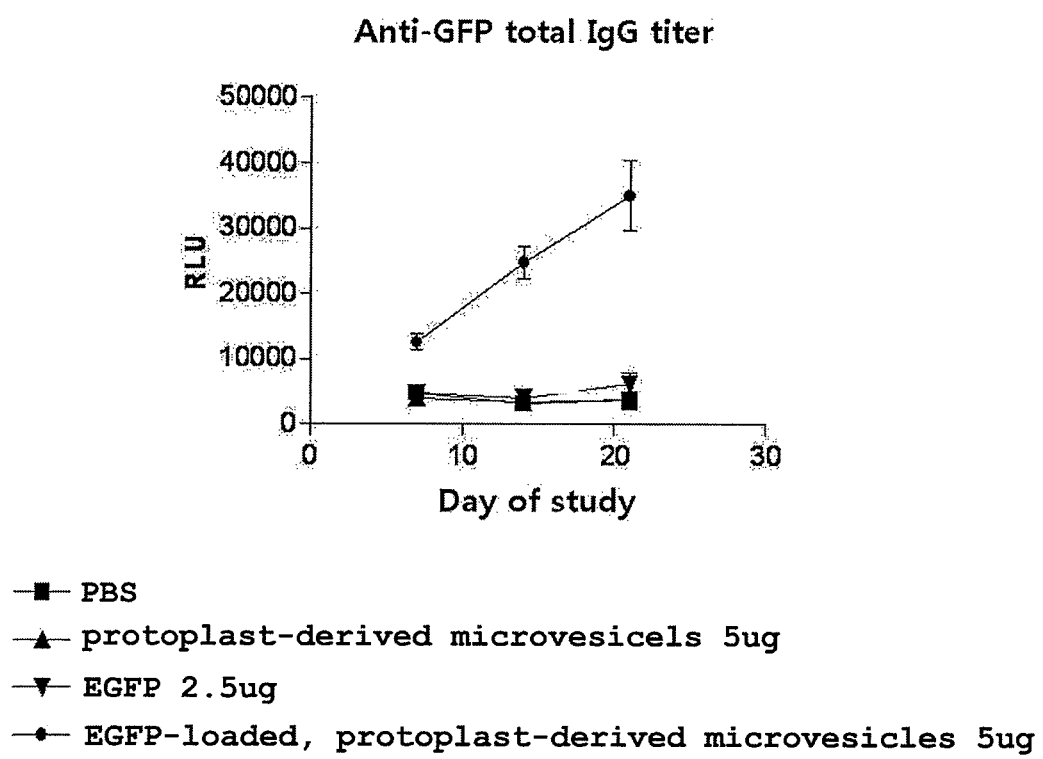
FIG. 14 is a graph showing the ability of antigen-loaded, protoplast-derived microvesicles to induce the production of an IgG antibody specific for the antigen in mice.
Figure 15:
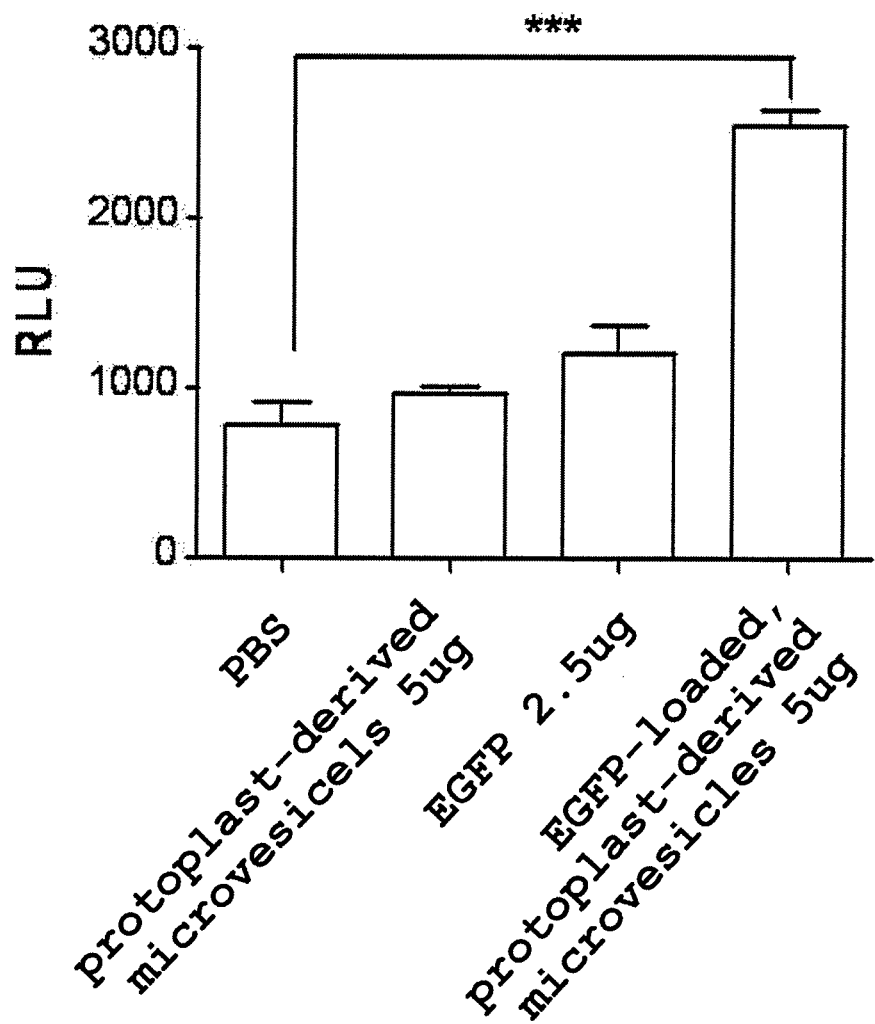
FIG. 15 is a graph showing the ability of antigen-loaded, protoplast-derived microvesicles to induce the production of an IgE antibody specific for the antigen in mice.

In FIGS. 14 and 15, RLU value of IgG and IgE specific for EGFP are shown, respectively. RLU value represents the relative amount of EGFP-specific antibody. As shown in FIGS. 14 and 15, mice produced IgG and IgE against EGFP when injected with the *E. coli* protoplast-derived microvesicles loaded with EGFP, but did not produce any antibody to EGFP when injected with EGFP or EGFP-void microvesicles.

Also, the formation of memory T cells was examined as follows. Cells were obtained by grinding the spleen excised three days after the final injection of the microvesicles, and suspended in 2.5% FBS in a DMEM buffer. Cells were obtained as a pellet by centrifugation at 1,000 rpm for 5 min. The cell pellet was resuspended in 5 mL of an RBC lysis buffer (0.15 M NH$_4$Cl, 10 mM KHCO$_3$, 0.1 mM Na$_2$EDTA, pH 7.2) to lyse erythrocytes. The suspension was centrifuged again at 1,000 rpm for 5 min to form a pellet of splenocytes. These splenocytes were seeded at a density of 1×10$^5$ cells/well into 48-well plates that were coated with 1 µg/ml antibodies to CD3 and CD28 on a previous day. Incubation at 37° C. for 12 hrs induced the expression of T cell cytokines. Thereafter, the cultures were centrifuged at 800×g for 10 min, and then at 3,000×g for 20 min, and the supernatants free of cells were taken.

The supernatants were subjected to the following experiments to examine whether memory T cells were formed in the vaccinated mice. 96-well plates were coated with the T cell cytokines IL-4, IFN-γ, IL-10, and IL-17, and blocked for 1 hr with 100 µl of 1% BSA/PBS per well. The supernatants of the conditioned media were diluted 1/10, and the dilutions were plated into the plates and incubated at room temperature for 2 hours. After incubation with a biotin-conjugated, detection antibody to the cytokines for 2 hours, the plates were washed with 0.05% Tween-20 in PBS. Treatment with streptavidin-POD for 20 min was followed by color development with a BM-POD substrate.

Figure 16:
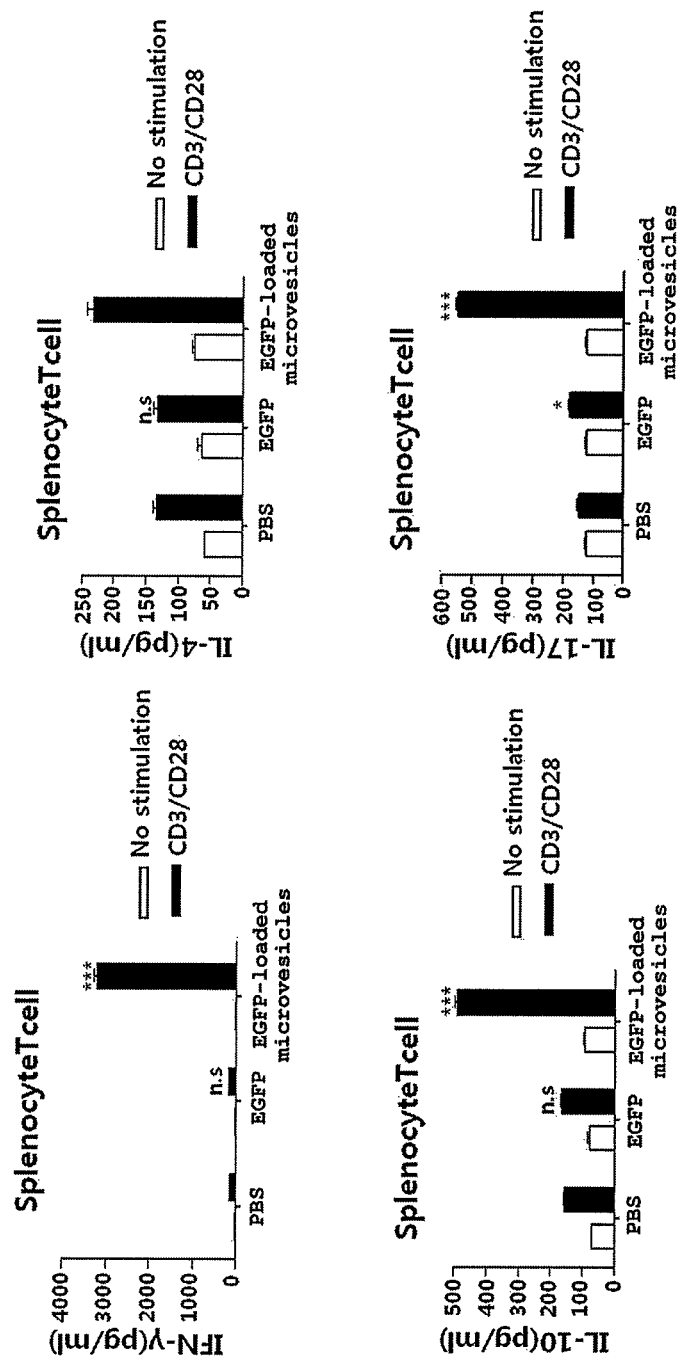
FIG. 16 shows graphs illustrative of the ability of antigen-loaded, protoplast-derived microvesicles to induce the production of memory T cells specific to the antigen in mice.

In FIG. 16, levels of the cytokines are analyzed as RLU values of the color developed. As is understood from the data of FIG. 16, the mice, when injected with the E. coli protoplast-derived microvesicles loaded with an EGFP protein, expressed IL-4, IFN-γ, IL-10, and IL-17, with the concomitant production of memory T cells responsible for the memory of immune responses.

These results indicate that the microvesicles can deliver proteins (antigens) encapsulated therein to immune cells, and induce antigen-specific immune responses in vivo.

Example 9

Preparation of Microvesicles Loaded with Bacterial Inclusion Body

When it is overexpressed artificially, OmpA, a bacterial outer membrane protein, is found as an inclusion body within the cell. Accordingly, artificially overexpressed OmpA can serve as an indicator of whether or not the microvesicles are loaded with an inclusion body.

An OmpA gene was inserted into pET-30a(+) to construct a recombinant vector called "pET-30a(+)-OmpA-His6."

E. coli BL21 was transformed with pET-30a(+)-OmpA-His6 by heat shock, incubated at 37° C. for 1 hr in 1 mL of LB broth, and grown at 37° C. for 16 hrs on LB agar plates containing kanamycin. Of the colonies formed on the plates, one was picked and tested with regard to whether it contained pET-30a(+)-OmpA-His6. The colony was inoculated into 20 mL of LB broth containing kanamycin, and grown at 37° C. to O.D$_{600}$=0.4 at which time the cells were induced at 37° C. for 3 hrs in the presence of 1 mM IPTG (isopropyl β-D-thiogalactopyranoside) to overexpress the fusion protein. That is, transformed bacteria in which OmpA-Histag was overexpressed were obtained.

Microvesicles, whether or not loaded with OmpA-Histag, were constructed using the methods described in Examples 1 and 2. Thereafter, 20 µg of each of the microvesicles was individually mixed with such an amount of a 5× loading dye that the concentration of the loading dye was diluted 1×. The mixtures were boiled at 100° C. for 5 min, and loaded into a 12% polyacrylamide gel. After electrophoresis at 80 V for 2 hrs, the proteins were transferred onto a PVDF membrane at 400 mA for 2 hrs. The membrane was blocked at 4° C. for 12 hrs in a 3% solution of skim milk in PBS. The membrane was treated at room temperature for 2 hrs with an anti-Hig-tag antibody, washed twice with PBS, and reacted at room temperature for 1 hr with a peroxidase-conjugated secondary antibody. It was washed again for 30 min with PBS, followed by visualization with an ECL substrate. The result is shown in FIG. 17.

Figure 17:
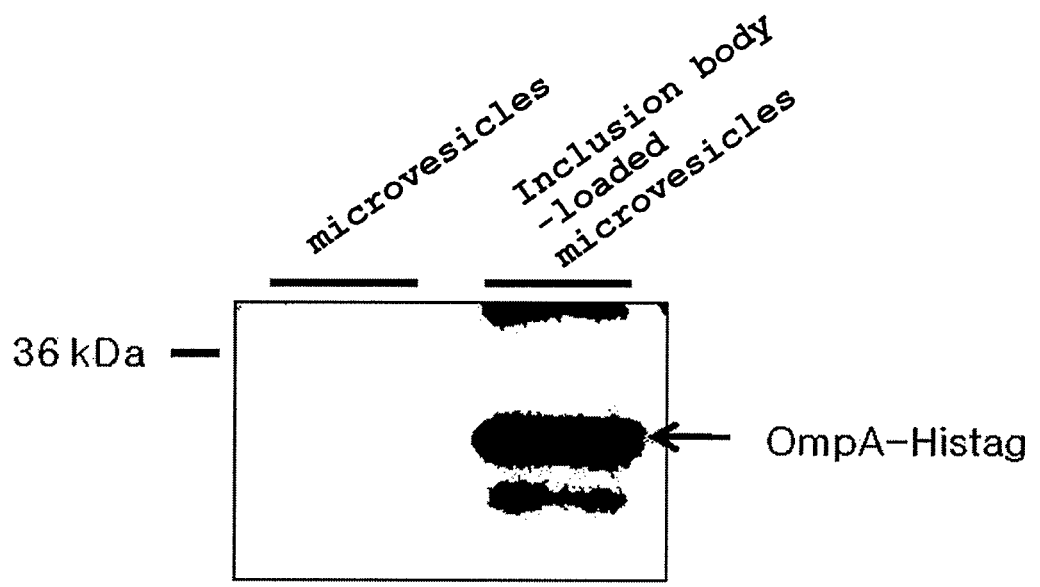
FIG. 17 is a view showing the capability of the protoplast-derived microvesicles to load an inclusion body thereto.

As can be seen in FIG. 17, the microvesicles constructed from the protoplast of the OmpA-Histag-overexpressing bacteria were detected by an anti-Histag antibody whereas the Histag protein was not detected in the microvesicles constructed from the protoplast of bacteria void of OmpA-Histag.

Hence, it was apparent from the result that the inclusion body was loaded to the microvesicles.

Example 10

Preparation of Microvesicles Loaded with Bacterial Outer Membrane Protein

E. coli was transformed in a manner similar to that of Example 9 to overexpress OmpA, OmpC, or OmpF. The transformed bacteria were mixed at a ratio of 1:1:1, and used to construct protoplast-derived microvesicles loaded with OmpA, OmpC, and OmpF, using the methods disclosed in Examples 1 and 2.

In order to examine whether the protoplast-derived microvesicles were loaded with all of OmpA, OmpC, and OmpF, and where OmpA, OmpC, and OmpF were positioned in the microvesicles, the following experiments were conducted. First, the bacterial protoplast-derived microvesicles were treated with trypsin to digest extravesicular domains of the membrane proteins. After denaturation of the trypsin at a high temperature, the microvesicles were lysed to expose intra- and extramembrane proteins to the solution, and then treated with an antibody specific for the His6 tag fused to OmpA, OmpC, and OmpF, each. The result is given in FIG. 18.

On the basis of the fact that trypsin cannot go across the protoplast, the microvesicles were treated with trypsin before and after the lysis thereof to examine the position where OmpA, OmpC, and OmpF proteins were expressed. If the proteins were positioned outside the microvesicles, they could not react with the antibody because they were digested. On the other hand, they could react with the antibody if positioned inside, even after the microvesicles were treated with trypsin.

Figure 18:
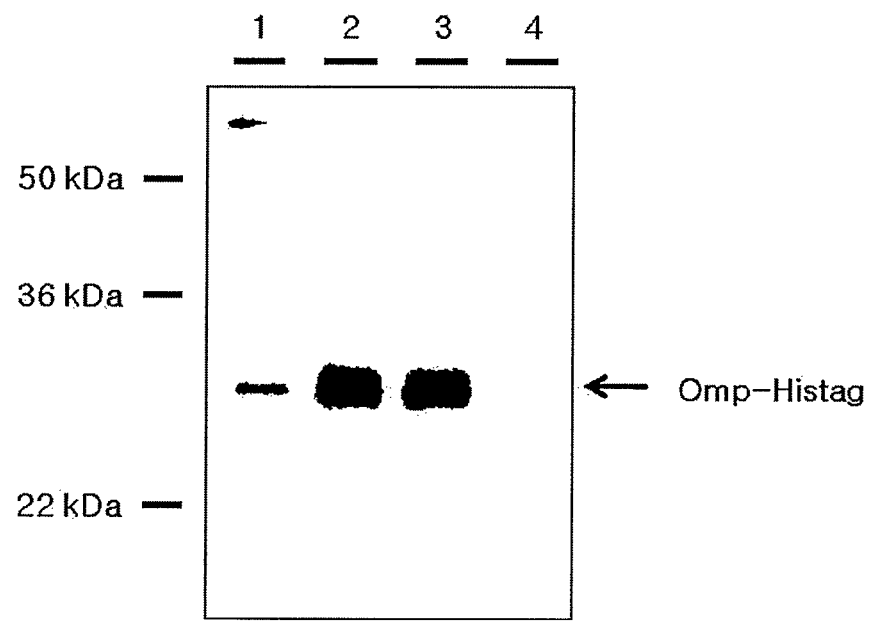
FIG. 18 is a view showing the capability of the protoplast-derived microvesicles to load an Omp protein thereto.

As is understood from the data of FIG. 18, an antigen-antibody complex was detected even after treatment with trypsin, meaning that almost all the OmpA, the OmpC, and the OmpF were located inside the microvesicles. This suggests the likelihood that if they are administered while being protected by a protoplast, OmpA, OmpC, and OmpF could evade inflammatory responses, but induce immune responses, thus exerting safe vaccine effects.

Example 11

Vaccine Activity of Microvesicles Loaded with Bacterial Outer Membrane Protein

Microvesicles loaded with bacterial outer membrane proteins were examined for vaccine activity. Protoplast-derived microvesicles loaded with OmpA, OmpC, and OmpF were intraperitoneally injected three times at a dose of 40 µg at regular intervals of seven days into mice. For a control, PBS was employed. An examination was made of the formation of an antibody specific for OmpA. Seven days after the final injection, blood samples were taken from the eyes of the mice, incubated at room temperature for 30 min, stored at 4° C. for 1 hr, and centrifuged at 1,300×g for 20 min. The supernatants free of cells were taken.

Each well of 96-well plates was coated with 50 ng of an OmpA protein, and blocked for 2 hr with 100 μl of 3% BSA/PBS. The supernatants from the mouse blood were diluted 1/1000, added to each well, and incubated at room temperature for 2 hrs, followed by incubation with an HRP-conjugated anti-mouse antibody for 1 hr. After washing with 0.05% Tween-20 in PBS, a color was developed with a BM-POD substrate.

Figure 19:
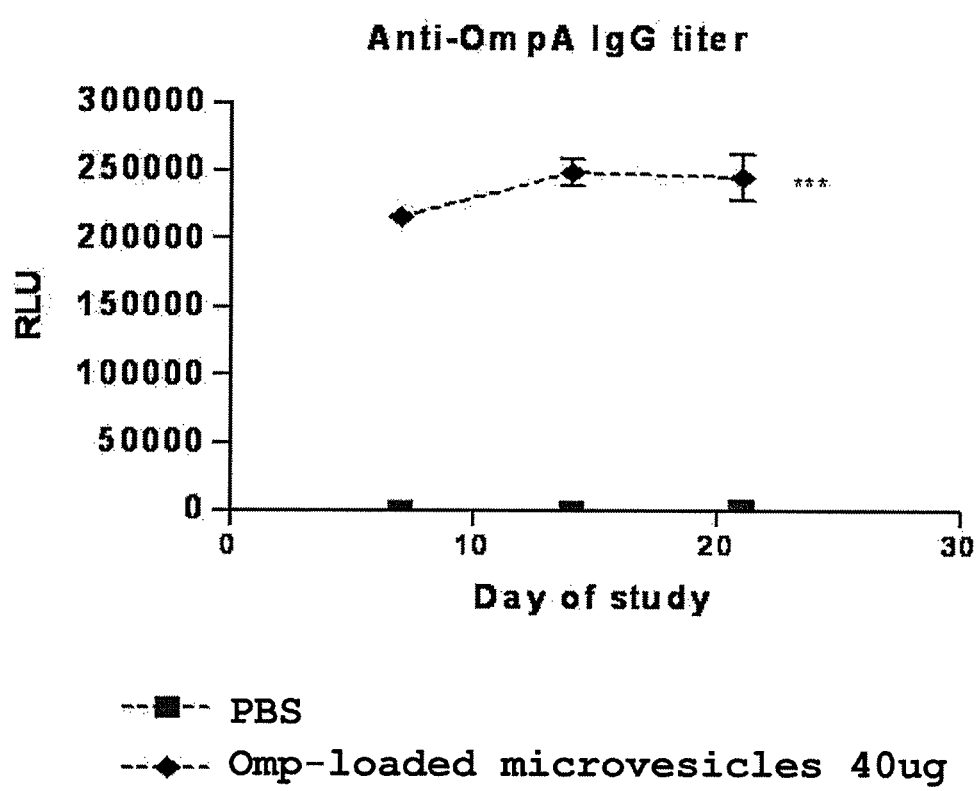
FIG. 19 is a graph showing that OmpA antigen-loaded, protoplast-derived microvesicles induce the production of an OmpA-specific IgG antibody in mice.

In FIG. 19, levels of the OmpA-specific antibody are analyzed as RLU values of the color developed.

As shown in FIG. 19, the mice produced an antibody to OmpA when injected with the protoplast-derived microvesicles loaded with the Omp protein.

In addition, an examination was made to see whether the immune response induced by the microvesicles had a vaccine effect on bacteria. *E. coli* C4 was grown to O.D=1.0 and diluted 1/10 in PBS. The dilution of the bacteria in PBS was intraperitoneally administered once at a dose of 100 μl to the mice seven days after the final injection of the microvesicles. Dead mice were counted every six hours.

Figure 20:
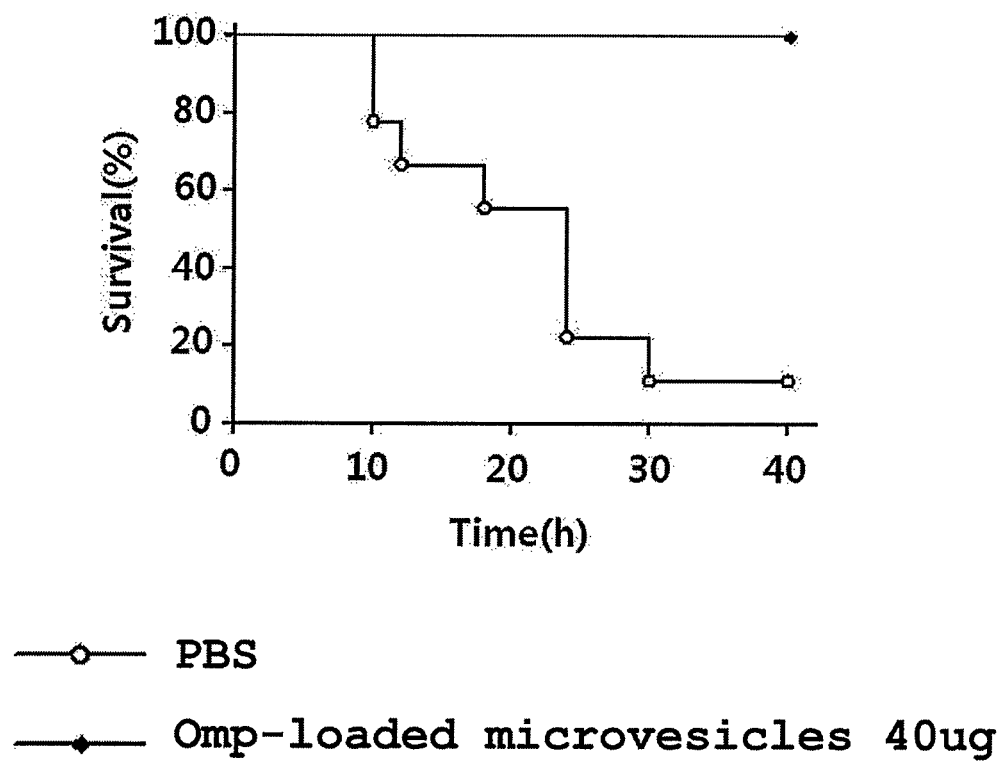
FIG. 20 is a graph showing that Omp antigen-loaded microvesicles act as a vaccine to bacteria.

FIG. 20 is a survival curve of mice with time after the bacterial cells were injected. As can be seen in the curve, all of the mice immunized with the microvesicles survived while 90% of the PBS group died, indicating that the protoplast-derived microvesicles can be used as a carrier for delivering an antigen, and induce an effective immune effect on subsequent bacterial infection.

Example 12

Preparation of Microvesicles Loaded with Melanoma Antigen

An examination was made with regard to whether the bacterial protoplast-derived microvesicles can serve as a carcinogenic antigen carrier for use in a vaccine against cancer by provoking an immune response to cancer cells. Bacterial cells were transformed with a gene encoding Mart-1, known as a carcinogenic protein causing melanoma.

For use in amplifying a Mart-1 gene, primers with specific restriction enzyme sites were synthesized on the basis of the base sequence of Mart-1 gene as follows.

```
Forward primer:
                                    (SEQ ID NO. 5)
5'-GGAATTCCATATGCCCCAAGAAGAC-3'

Reverse primer:
                                    (SEQ ID NO. 6)
5'-AGGCGTCGACTCAGGGTGAATAAGG-3'
```

(Bold Letters Indicate NdeI, and SalI Restriction Sites)

PCR was performed using the primers with the genomic DNA of the mouse melanoma cell B16BL6 serving as a template. The PCR product thus obtained was purified using a Quiaquick gel purification kit. Following digestion at 37° C. for 8 hrs with the restriction enzymes NdeI and SalI, and subsequent purification with a Quiaquick PCR purification kit, the amplified gene was ligated to a pET-30a(+) vector which had been previously digested with the same restriction enzymes. The resulting recombinant vector was named "pET-30a(+)-Mart-1-His6."

The recombinant vector pET-30a(+)-Mart-1-His6 was transformed into *E. coli* BL21 by heat shock and was then incubated at 37° C. for 1 hr in 1 mL of LB broth, and grown at 37° C. for 16 hrs on LB agar plates containing kanamycin. Of the colonies formed on the plates, one was picked and tested with regard to whether it contained pET-30a(+)-Mart-1-His6. The colony was inoculated into 20 mL of LB broth containing kanamycin, and grown at 37° C. to $O.D_{600}$=0.4 at which time the cells were induced at 37° C. for 3 hrs in the presence of 1 mM IPTG to express Mart-1.

Microvesicles loaded with the Mart-1 protein were constructed using the methods described in Examples 1 and 2.

An examination was made of the translation of the Mar-1 protein within the microvesicle. For this, 20 μg of each of a whole cell lysate of the B16BL6 cell line, the Mart-1-loaded microvesicles, and the unloaded microvesicles was individually mixed with such an amount of a 5× loading dye that the concentration of the loading dye was diluted 1×. The mixtures were boiled at 100° C. for 5 min, and loaded into a 12% polyacrylamide gel. After electrophoresis at 80 V for 2 hrs, the proteins were transferred onto a PVDF membrane at 400 mA for 2 hrs. The membrane was blocked at 4° C. for 12 hrs in a 3% solution of skim milk in PBS. The membrane was treated at room temperature for 2 hrs with an anti-Mart-1 antibody, washed twice with PBS, and reacted at room temperature for 1 hr with a peroxidase-conjugated secondary antibody. It was washed again for 30 min with PBS, followed by visualization with an ECL substrate. The result is shown in FIG. 21.

Figure 21:
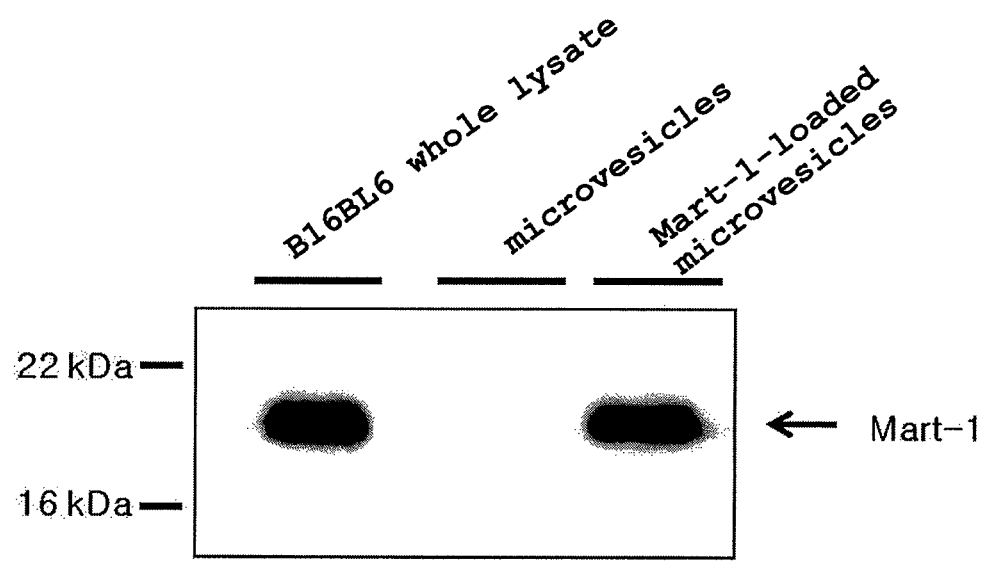
FIG. 21 is a view showing the melanoma antigen Mart-1 loaded to protoplast-derived microvesicles.

As can be seen in FIG. 21, the microvesicles constructed from the protoplast of the Mart-overexpressing bacteria were detected by an anti-Mart-1 antibody, whereas the Mart-1 protein was not detected in the microvesicles constructed from the protoplast of bacteria void of Mart-1.

Example 13

Vaccine Effect of Melanoma Antigen-Loaded Microvesicles on Melanoma

The Mart-1-loaded microvesicles prepared in Example 12 were intraperitoneally injected at a dose of 25 μg three times at regular intervals of seven days. The mouse melanoma cell line (B16BL6) was subcutaneously injected at a dose of 1×10$^6$ cells into the mice seven days after the third injection. The cancer tissue formed for 20 days was excised from the mice, and weighed.

Figure 22:
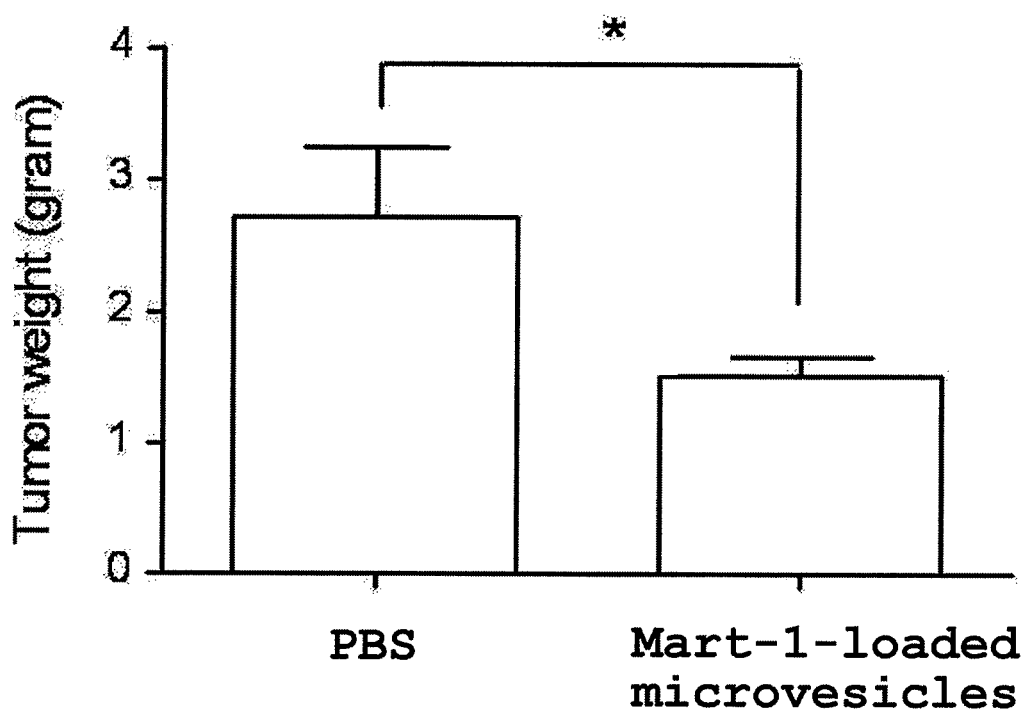
FIG. 22 is a graph showing the vaccine effect of Mart-1-loaded, protoplast-derived microvesicles on melanoma.

As can be seen in FIG. 22, the cancer tissue excised from the mice injected with the Mart-1 protein-loaded microvesicles weighed less than that excised from the mice injected with PBS.

From the results obtained above, it was apparent that the protoplast-derived microvesicles can be used as a carrier for a carcinogenic antigen, thereby provoking an immune response to cancer.

Example 14

Preparation of Bacterial Protoplast-Derived Microvesicle Loaded with EGF Fusion Protein A human EGF protein was loaded onto the surface of a protoplast by use of the bacterial inner membrane protein PrsA. For this, gene coding for a polypeptide extending from the N-terminus to position 290 of the amino acid sequence of PrsA was amplified using stop codon-free primers which were synthesized on the basis of a known base sequence of PrsA, with restriction enzyme sites set therein.

```
Forward primer:
                                    (SEQ ID NO. 7)
5'-CATATGAAGAAAATCGCAATAGCAG-3'

Reverse primer:
                                    (SEQ ID NO. 8)
5'-TCTAGATTTAGAATTGCTTGAAGATGAAG-3'
```

(Bold Letters Denote NdeI and XbaI Recognition Sites)

PCR was performed on the genomic DNA of *B. subtilis* in the presence of the primers, and the PCR product thus obtained was purified from the PCR band using a Quiaquick gel purification kit. The purified product was digested at 37° C. for 8 hrs with the restriction enzymes NdeI and XbaI, and purified again with a Quiaquick PCR purification kit before ligation to the pHCE vector digested with the same enzymes. The resulting recombinant vector was named "pHCE-prsA."

For use in fusion into the pHCE-prsA vector, a human EGF gene was amplified using primers which had been synthesized on the basis of a base sequence of a human EGF gene, with specific restriction enzyme sites set therein.

```
Forward primer:
                                    (SEQ ID NO. 9)
5'-GCTCTAGAAATACTGACTCTGA ATGTCCC-3'

Reverse primer:
                                    (SEQ ID NO. 10)
5'-CAAGCTTTCAGCGCAGTTCC CACCACTTC-3'
```

(Bold Letters Denotes XbaI, and HindII Restriction Sites)

PCR was performed on the genomic DNA of the human non-small cell cancer cell line A549 in the presence of the primers, and the PCR product thus obtained was purified from the PCR band using a Quiaquick gel purification kit. The purified product was digested at 37° C. for 8 hrs with the restriction enzymes XbaI and HindIII, and purified again with a Quiaquick PCR purification kit before ligation to the pHCE-prsA vector digested with the same enzymes. The resulting recombinant vector was named "pHCE-prsA-EGF."

Following transformation with the pHCE-prsA-EGF vector by heat shock, *E. coli* DH5α was incubated at 37° C. for 1 hr in 1 mL of LB broth, and grown at 37° C. for 16 hrs on LB agar plates containing ampicillin. Of the colonies formed on the plates, one was picked, and examined by colony-PCR and restriction enzyme mapping with regard to whether it contained pHCE-prsA-EGF.

From the Gram-negative bacterium *E. coli* that had been transformed with the pHCE-prsA-EGF vector or that had not been transformed, microvesicles loaded with the EGF fusion protein, or unloaded microvesicles, were constructed using the methods disclosed in Examples 1 and 2. Thereafter, 20 μg of each of the microvesicles was individually mixed with such an amount of a 5× loading dye that the concentration of the loading dye was diluted 1×. The mixtures were boiled at 100° C. for 5 min, and loaded into a 12% polyacrylamide gel. After electrophoresis at 80 V for 2 hrs, the proteins were transferred onto a PVDF membrane at 400 mA for 2 hrs. The membrane was blocked for 2 hrs in a 3% solution of skim milk in PBS. The membrane was treated at 4° C. for 12 hrs with an anti-EGF antibody, washed twice with PBS, and reacted at room temperature for 1 hr with a peroxidase-conjugated secondary antibody. It was washed again for 30 min with PBS, followed by visualization with an ECL substrate. The result is shown in FIG. 23.

Figure 23:
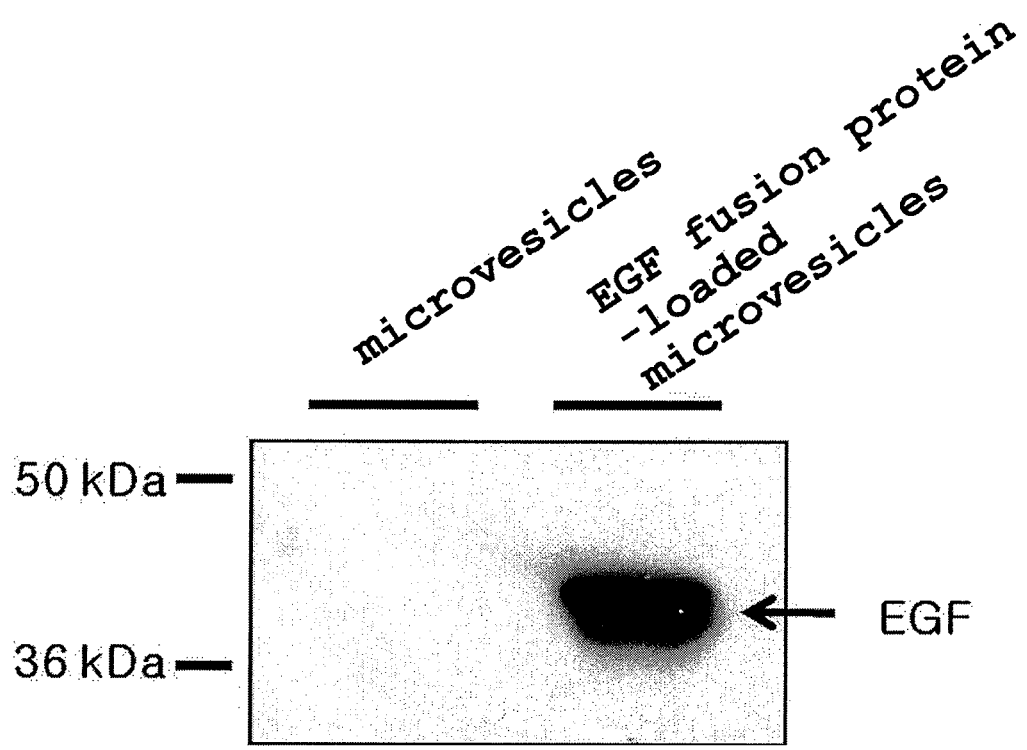
FIG. 23 is a view showing an EGF fusion protein loaded to protoplast-derived microvesicles.

As can be seen in FIG. 23, the microvesicles constructed from the protoplast of the EGF fusion protein-overexpressing bacteria were detected by an anti-EGF antibody, whereas the EGF protein was not detected in the microvesicles constructed from the protoplast of bacteria void of the EGF fusion protein.

The result indicates that microvesicles loaded with the EGF fusion protein were constructed correctly.

Trypsin was used to examine whether the EGF fusion protein was located on the outer surface of the microvesicles. On the basis of the fact that trypsin cannot go across the protoplast, the microvesicles were treated with trypsin to digest extravesicular domains of cell membrane proteins before examining the activity of the EGF fusion protein. After denaturation of the trypsin at a high temperature, the microvesicles were lyzed to expose internal and transmembrane proteins to the solution, and then treated with an antibody specific for EGF. The result is given in FIG. 24.

Figure 24:
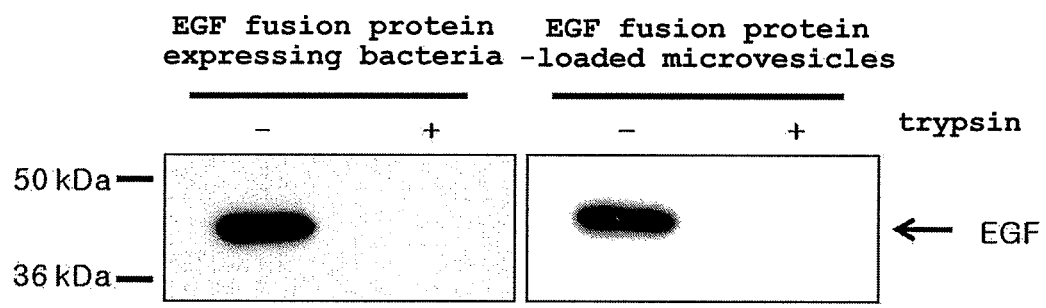
FIG. 24 is a view showing that an EGF fusion protein is loaded to the surface of the protoplast-derived microvesicles while retaining accurate topology.

In FIG. 24, '+' and '−' stand for treatment with and without trypsin, respectively.

As can be seen in FIG. 24, the EGF antibody was not detected upon trypsinization, which makes it possible to infer that the EGF domain of the EGF fusion protein is directed outside the microvesicles, and that the microvesicles loaded with the EGF fusion protein can specifically target the cells expressing an EGF receptor.

Example 15

In Vitro Assay for Cell Specific Delivery of EGF Fusion Protein-Loaded Microvesicles For use in examining in vitro the cell-specific delivery of the EGF fusion protein-loaded microvesicles, the human non-small cell lung cancer cell line A549 was seeded at a density of $2 \times 10^4$ cells/well on 24-well plates, and then incubated for 24 hours. In A549 cells, an EGF receptor is abundantly found on the cell membrane.

From the protoplasts of *E. coli* or EGF-expressing *E. coli* prepared in Example 10, microvesicles were prepared using the methods described in Examples 1 and 2. DiI (1,1'-dioctadecyl-3,3,3'3'-tetramethylindocarbocyanine perchlorate, Invitrogen, No. V22885) was added at a final concentration of 5 μM to the *E. coli* protoplast-derived microvesicles, and incubated at room temperature for 30 min. DiI is a red fluorescent dye.

The cells were washed twice with PBS, and 500 μl of a medium was added to each well of the plates where the cells were plated, followed by incubation with 10 μg/ml of the DiI-labeled microvesicles for 20 min.

Again, the cells were washed with PBS, and 500 μl of a serum-free medium and Cell Tracker solution at a final concentration of 5 μM was added to each well before incubation for 30 min. The cells were washed again with PBS, and incubated for 30 min in 500 μl of a serum-supplemented medium in each well. The cover glass was fixed at room temperature for 10 min with 500 μl of 4% paraformaldehyde in each well, and observed under a confocal microscope. Microvesicles labeled with DiI were observed to appear red fluorescent at a rhodamine wavelength, while cells with GFP were visualized green fluorescent at FITC wavelengths. The cells and the microvesicles were counted, and the number of microvesicles per cell was calculated. The results are given in FIG. 25.

Figure 25:
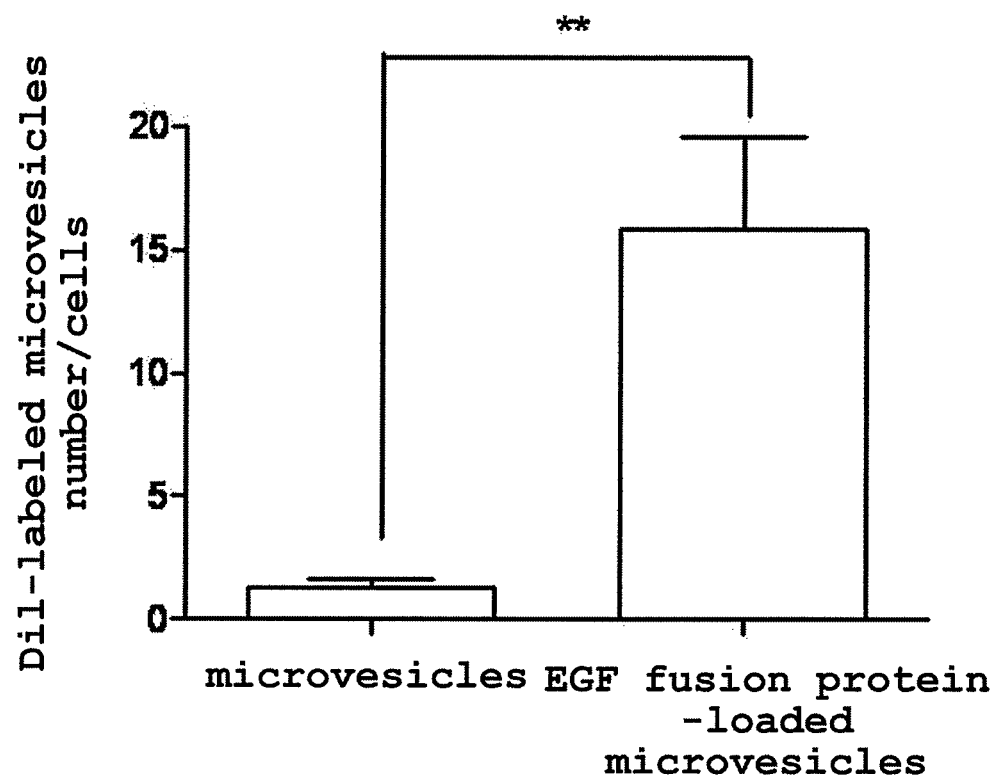
FIG. 25 is a graph showing the selective delivery of an EGF fusion protein loaded to microvesicles to cells of interest.

As can be seen in FIG. 25, the number of microvesicles that bound to A549 cells was about 1.2 per cell when they were derived from the EGF-void *E. coli* protoplasts, but increased to about 7.9 per cell when they were derived from EGF-loaded *E. coli* protoplasts.

These results make it possible to infer that EGF-loaded microvesicles can selectively fuse to the cells expressing EGF receptors on the cell membrane, like A549.

In addition, an examination was made to see whether the binding of the microvesicles to the cells was due to the specific interaction of the EGF-EGF receptor. The mouse colon carcinoma cell line CT26 was seeded at a density of $2 \times 10^6$ cells/well into 12-well plates, and incubated for 24 hrs. CT26 expresses a murine EGF receptor on the cell membrane, and can be bound to human EGF. The cells were washed twice with PBS, and 500 µl of a medium was added to each well of the plates, followed by incubation with 100 ng/ml EGF for 30 min to leave no unbound EGF receptors. Excess EGF proteins were washed off with PBS, and the cells were incubated for 20 min with 10 µg/ml of the DiI-labeled microvesicles.

The cells were washed again with PBS, and incubated for 30 min in 500 µl of a serum-supplemented medium in each well. The cover glass was fixed at room temperature for 10 min with 500 µl of 4% paraformaldehyde in each well. Microvesicles labeled with DiI were observed to appear red fluorescent at a rhodamine wavelength under a fluorescence microscope.

Figure 26:
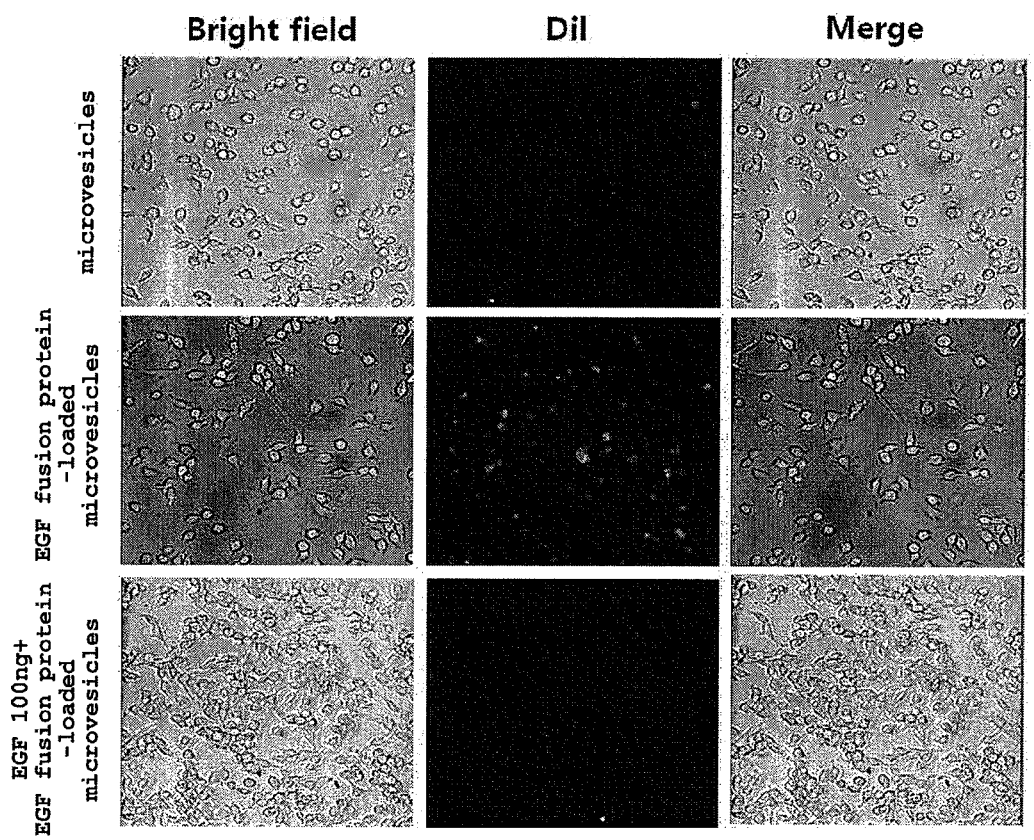
FIG. 26 shows images illustrative of the delivery of an EGF fusion protein loaded to microvesicles under the guidance of EGF.

When the EGF receptors were already occupied by free EGF proteins, as can be seen in FIG. 26, the red fluorescent signals indicative of the entry of the microvesicles into the cells disappeared, in contrast to the case where the EGF receptors were not treated with free EGF proteins in advance.

The data obtained above indicates that microvesicles loaded with the EGF fusion protein can specifically fuse to cells expressing an EGF receptor through interaction between EGF and EGF receptor.

Example 16

Intracellular Signal Transduction of EGF Fusion Protein-Loaded Microvesicles

The human non-small cell lung cancer cell line A549 was seeded at a density of $1 \times 10^5$ cells/well on 6-well plates and then incubated for 16 hrs. The cells were washed twice with PBS, and cultured for 16 hrs in a serum-free medium. Then, the cells were incubated for 10 min with 10 µg/ml of the EGF fusion protein-loaded microvesicles or the unloaded microvesicles, prepared in Example 14. The A549 cells were washed with PBS, and lysed in 150 µl of M-PER (Pierce) containing a phosphatase inhibitor in each well to afford whole cell lysates.

Thereafter, 20 µg of each of the whole cell lysates was individually mixed with such an amount of a 5× loading dye that the concentration of the loading dye was diluted 1×. The mixtures were boiled at 100° C. for 5 min, and loaded into a 10% polyacrylamide gel. After electrophoresis at 80 V for 2 hrs, the proteins were transferred onto a PVDF membrane at 400 mA for 2 hrs. The membrane was blocked for 2 hrs in a 3% solution of skim milk in TBS. The membrane was treated at 4° C. for 12 hrs with an EGF receptor antibody, a phosphor-EGF receptor antibody, an Erk antibody, or a phosphor-Erk antibody, washed twice with TBS, and reacted at room temperature for 1 hr with a peroxidase-conjugated secondary antibody. It was washed again for 30 min with TBS, followed by visualization with an ECL substrate. The result is shown in FIG. 27.

Figure 27:
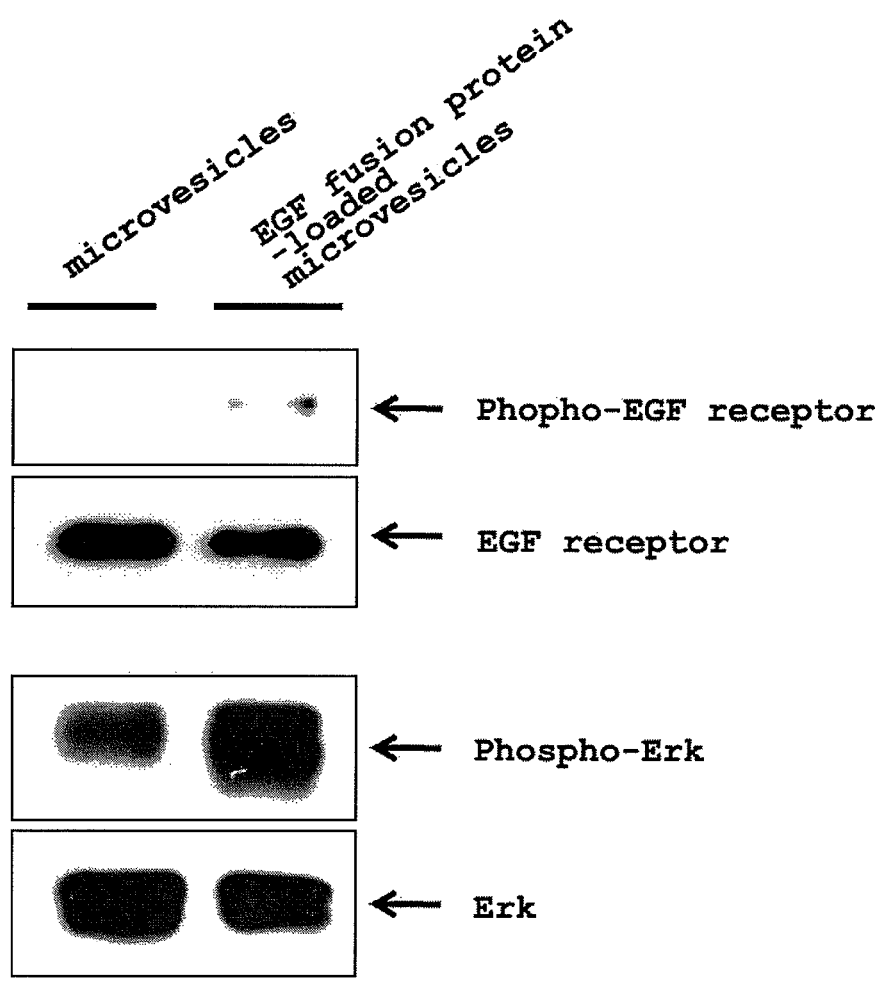
FIG. 27 shows images illustrative of the EGF signal transduction by microvesicles loaded with an EGF fusion protein.

As can be seen in FIG. 27, treatment with the EGF fusion protein-loaded microvesicles triggered the EGF signaling pathway by inducing the phosphorylation of the EGF receptor, which, in turn, stimulates the downstream signaling cascade, e.g., the phosphorylation of Erk. The EGF receptor and the Erk protein were used as controls.

These results make it possible to infer that the EGF fusion protein-loaded microvesicles can bind to the EGF receptor.

Example 17

Preparation of Microvesicles Loaded with Both Anticancer Drug and EGF Fusion Protein and In Vivo Assay for Selective Delivery EGF fusion protein-loaded microvesicles were prepared according to the method of Example 14, and mixed well and incubated at 4° C. for 12 hrs with 400 µg/ml doxorubicin, an anticancer drug. Thereafter, the suspension was ultracentrifuged at 100,000×g for 2 hrs. The pellet was resuspended in TBS to afford doxorubicin-loaded microvesicles.

The human lung cancer cell line A431 that overexpresses an EGF receptor was subcutaneously injected at a dose of $1 \times 10^6$ to mice, and cultured for 7 days. Seven days after the implantation of cancer cells, PBS, PBS containing 50 µg of the doxorubicin-loaded microvesicles, PBS containing 50 µg of the microvesicles loaded with both doxorubixin and the EGF fusion protein, or PBS containing 80 µg of doxorubicin was injected via the tail vein into the mice. The cancer tissue was excised from mice 6 hours after the injection, and was fixed for 24 hours in 4% paraformaldehyde. For dehydration, the fixed cancer tissue was immersed once in 70% ethanol, four times in 95% ethanol, three times in 100% ethanol, and three times in 100% xylene, each time for one hour in all cases. Thereafter, the tissues were embedded in paraffin, sectioned into slices 4 µm thick, and attached onto slide glass. The paraffin was melted by incubation at 60° C. for one hr. For hydration, the tissues were immersed three times in 100% xylene, four times in 100% ethanol, and three times in 95% ethanol, each time for one min in all cases, followed by storage for 5 min in flowing water.

After the hydration, the tissues were subjected to immunohistochemistry. In this regard, antigen retrieval was performed using a microwave method. The tissues were placed in 10 mM sodium citrate buffer (Sigma, No. S4641) and irradiated three times, each for five min, with microwaves. The tissues were cooled with flowing water, and blocked for two hrs with TBS (Tris Buffered Saline) containing 5% horse serum and 0.02% Triton X-100. An antibody (SantaCruz, No. SC1506) recognizing the endothelial marker CD31 was mixed at a ratio of 1:200 with TBS containing 5% horse serum and 0.02% Triton X-100, followed by incubation at 4° C. for 12 hours. The tissues were washed three times with TBS containing 0.02% Triton X-100, and incubated at room temperature for 1 hr with a green fluorescent Alexa 488-conjugated secondary antibody. They were washed three times with TBS containing 0.02% Triton X-100, and stained for 10 min with 5 µM of a host dye. The tissues were washed five times with TBS and the cover glass was underlayered with slide glass and observed under a confocal microscope. In the images, green-stained regions were measured.

Figure 28:
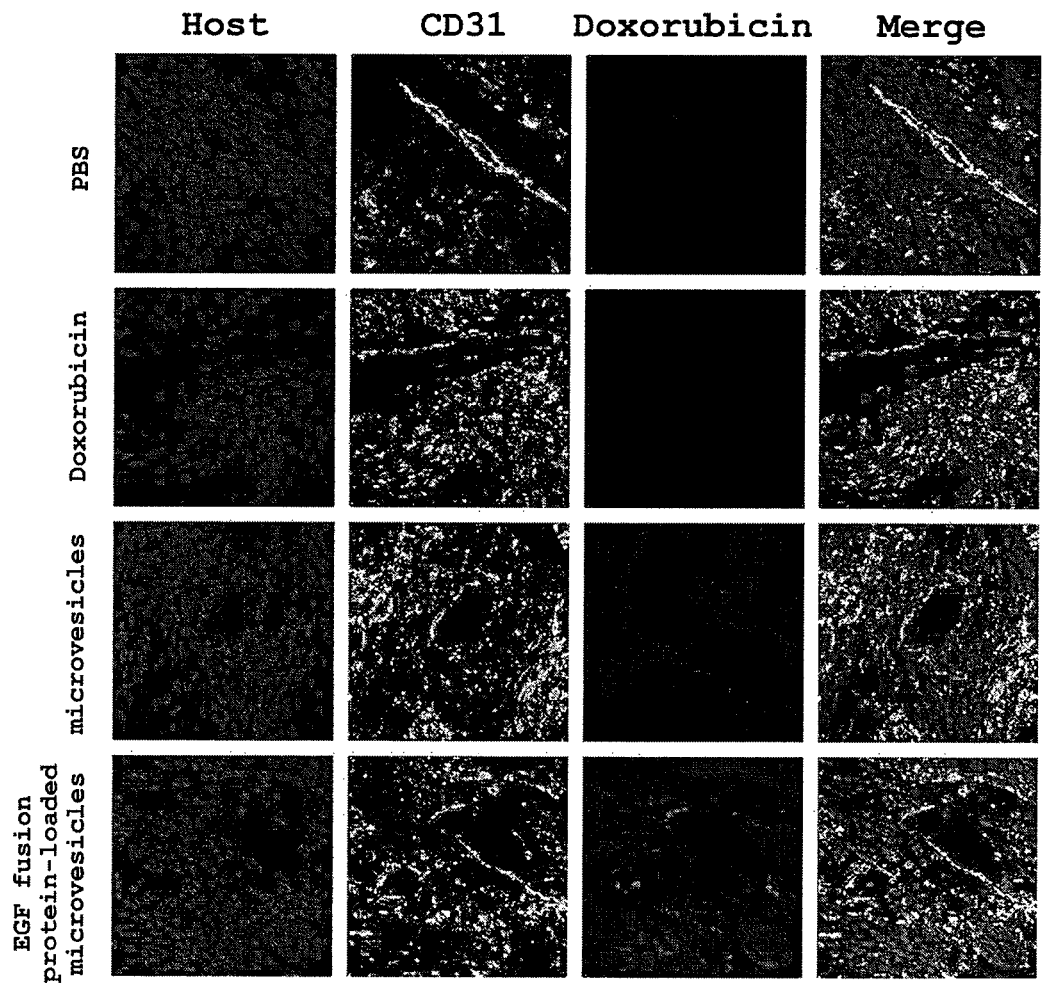
FIG. 28 shows images illustrative of the EGF fusion protein-loaded, microvesicle-mediated delivery of doxorubicin to a cancer tissue of interest in mice.

FIG. 28 shows microscopic images of cancer tissues in mouse groups. As can be seen in FIG. 28, doxorubicin was observed in the cancer tissue taken from the mice injected with the microvesicles loaded with both EGF fusion protein and doxorubicin, indicating that the EGF fusion protein plays an important role in selectively delivering doxorubicin to the cancer cells.

Taken together, the data obtained above demonstrates that the EGF fusion protein-loaded microvesicles specifically target cancer cells expressing an EGF receptor.

Example 18

Ability of EGF Fusion Protein-Loaded Microvesicles to Induce Antibody Formation

The EGF fusion protein-loaded microvesicles prepared using the method disclosed in Example 14 were intraperitoneally injected at a dose of 20 µg to mice, with PBS serving as a control. Seven days after injection, an examination was made of the formation of an antibody specific for the EGF protein. Blood samples were taken from the eyes of the mice, incubated at room temperature for 30 min, stored at 4° C. for 1 hr, and centrifuged at 1,300×g for 20 min. The supernatants free of cells were taken.

Each well of 96-well plates was coated with 50 ng of an EGF protein, and blocked for 2 hr with 100 µl of 1% BSA/PBS. The supernatants from the mouse blood were diluted 1/1000, added to each well, and incubated at room temperature for 2 hrs, followed by incubation with an HRP-conjugated anti-mouse antibody for 1 hr. After washing with 0.05% Tween-20 in PBS, a color was developed with a BM-POD substrate.

Figure 29:
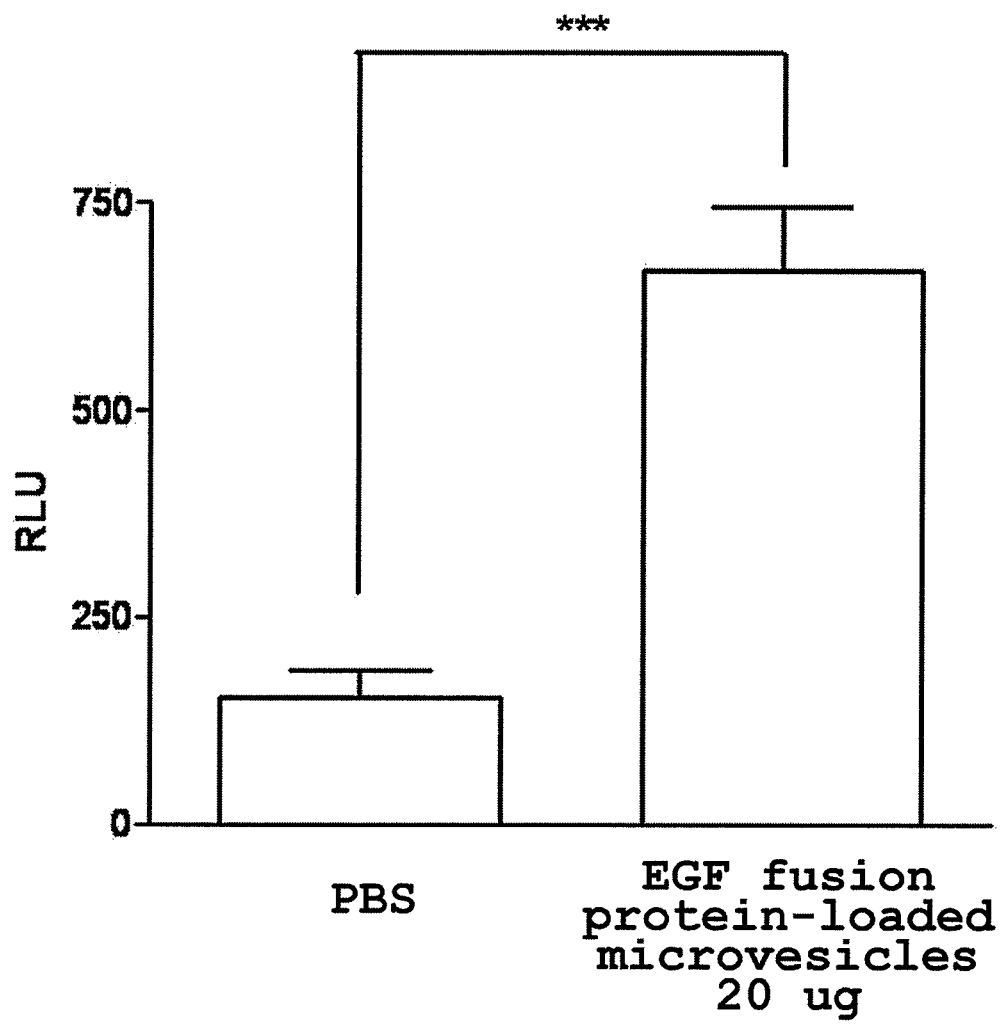
FIG. 29 is a graph showing the induction of an EGF-specific antibody by EGF fusion protein-loaded microvesicles in mice.

In FIG. 29, RLU values of the EGF-specific antibody are shown. RLU value represents the relative amount of EGFP-specific antibody. As can be seen in FIG. 29, mice produced antibodies against EGF when injected with the protoplast-derived microvesicles loaded with the EGF fusion protein.

These results indicate that when the protoplast-derived microvesicles deliver their loads to cells, the loads, whether located on the surface or the inside of the microvesicles, may act as antigens so as to provoke antibody formation.

Example 19

Preparation of Bacterial Protoplast-Derived Microvesicles Loaded with EGF Receptor Fusion Protein A human EGF receptor protein was loaded onto the surface of a protoplast by use of the bacterial inner membrane protein PrsA. For this, the pHCE-prsA vector, prepared in Example 14, carrying a gene coding for a polypeptide extending from the N-terminus to position 290 of the amino acid sequence of PrsA was employed.

For use in fusion to the pHCE-prsA vector, a human EGF gene was amplified using primers which had been synthesized on the basis of a base sequence of human EGF gene, with specific restriction enzyme sites set therein.

```
Forward primer:
                                      (SEQ ID NO. 11)
5'-GCCTCTAGACTGGAGGAAAAGAAAGTTTGC-3'

Reverse primer:
                                      (SEQ ID NO. 12)
5'-CCAAGCTTCAGGACGGGATCTTAGGC-3'
```

(Bold Letters Denotes XbaI, and HindII Restriction Sites)

PCR was performed on the genomic DNA of the human non-small cell cancer cell line A549 in the presence of the primers, and the PCR product thus obtained was purified from the PCR band using a Quiaquick gel purification kit. The purified product was digested at 37° C. for 8 hrs with the restriction enzymes XbaI and HindIII, and purified again with a Quiaquick PCR purification kit before ligation to the pHCE-prsA vector digested with the same enzymes. The resulting recombinant vector was named "pHCE-praA-EGFR."

Following transformation with the pHCE-prsA-EGFR vector by heat shock, *E. coli* DH5α was incubated at 37° C. for 1 hr in 1 mL of LB broth, and grown at 37° C. for 16 hrs on LB agar plates containing ampicillin. Of the colonies formed on the plates, one was picked, and examined by colony-PCR and restriction enzyme mapping with regard to whether it contained pHCE-prsA-EGFR.

From the Gram-negative bacterium *E. coli* that had been transformed with the pHCE-prsA-EGFR vector or that had not been transformed, microvesicles loaded with the EGF fusion protein, or unloaded microvesicles were constructed using the methods disclosed in Examples 1 and 2. Thereafter, 20 µg of each of the microvesicles was individually mixed with such an amount of a 5× loading dye that the concentration of the loading dye was diluted 1×. The mixtures were boiled at 100° C. for 5 min, and loaded into a 12% polyacrylamide gel. After electrophoresis at 80V for 2 hrs, the proteins were transferred onto a PVDF membrane at 400 mA for 2 hrs. The membrane was blocked for 2 hrs in a 3% solution of skim milk in PBS. The membrane was treated at 4° C. for 12 hrs with an anti-EGF antibody, washed twice with PBS, and reacted at room temperature for 1 hr with a peroxidase-conjugated secondary antibody. It was washed again for 30 min with PBS, followed by visualization with an ECL substrate. The result is shown in FIG. 30.

Figure 30:
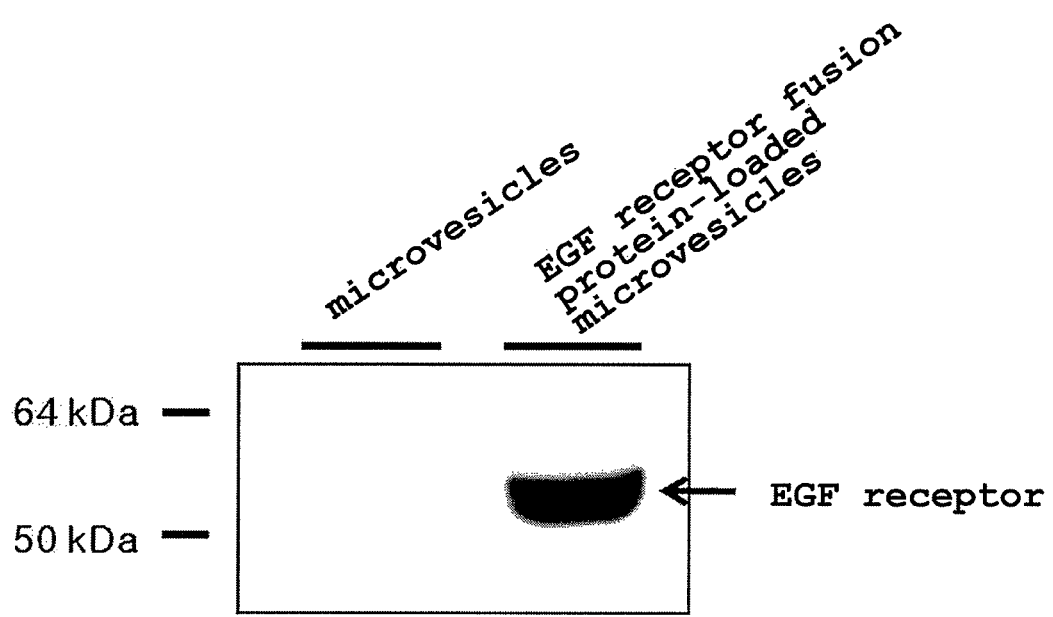
FIG. 30 illustrates the loading of an EGF receptor fusion protein to protoplast-derived microvesicles.

As can be seen in FIG. 30, the microvesicles constructed from the protoplast of the EGF receptor fusion protein-overexpressing bacteria were detected by an anti-EGF receptor antibody, whereas the EGF receptor fusion protein was not detected in the microvesicles constructed from the protoplast of bacteria void of the EGF receptor fusion protein.

The result indicates that microvesicles loaded with the EGF receptor fusion protein were constructed correctly.

Example 20

Binding of EGF to Bacterial Protoplast-Derived Microvesicles Loaded with EGF Receptor Fusion Protein Microvesicles loaded with the EGF receptor fusion protein prepared in Example 19, and unloaded microvesicles were constructed. Each microvesicle was placed in an amount of 0, 25, or 100 ng/well in 96-well plates, and incubated at room temperature for 12 hrs or longer so that they were allowed to attach to the wells. After the microvesicles were fixed for 1 hr in 100 µl of 1% BSA/PBS in each well, biotin-conjugated EGF was added in an amount of 100 ng/ml, and incubated for 2 hrs. The plates were washed with 0.05% Tween-20 in PBS, and treated with streptavidin-POD for 20 min, followed by color development with a BM-POD substrate.

Figure 31:
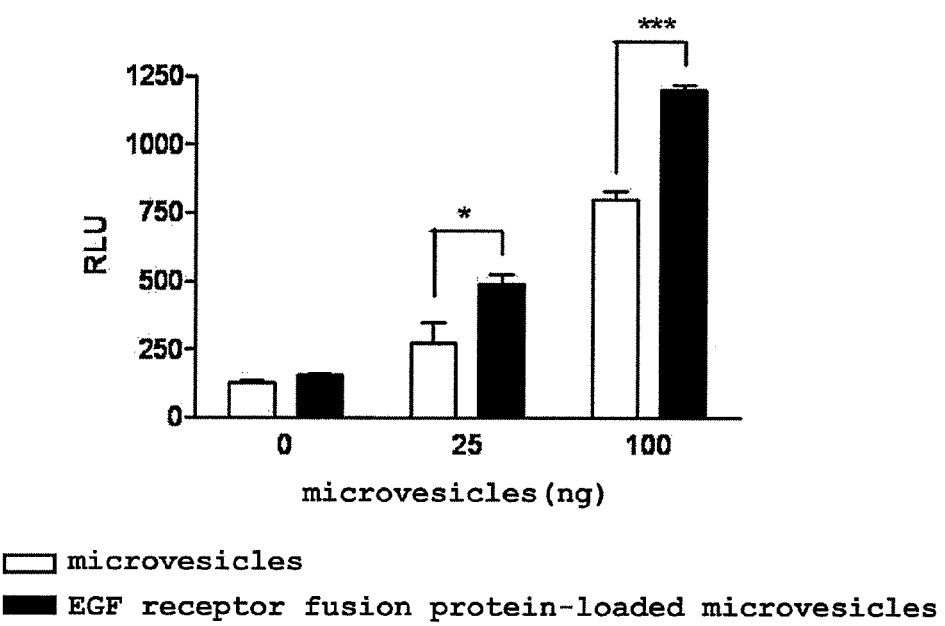
FIG. 31 is a graph showing the affinity of microvesicles loaded with an EGF receptor fusion protein for EGF.

In FIG. 31, levels of the EGF bound to the microvesicles are analyzed as RLU values of the color developed. As is understood from the data of FIG. 31, higher RLU values were detected in the EGF receptor fusion protein-loaded microvesicles bound to EGF, compared to the microvesicles void of the EGF receptor fusion protein.

These results indicate that the microvesicles loaded with the EGF receptor fusion protein can bind EGF.

Example 21

Preparation of Bacterial Protoplast-Derived Microvesicles Loaded with His-Tag Fusion Protein A His-tag protein was loaded onto the surface of a protoplast by use of the bacterial inner membrane protein PrsA. For this, the pHCE-prsA vector was digested with the restriction enzymes NdeI and HindIII at 37° C. for 8 hrs, and the disgest was purified using a Quiaquick gel purification kit, and inserted into a pET-30a(+) vector carrying His-tag which was previously treated with the same restriction enzymes. The resulting recombinant vector was named "pET-30a(+)-praA-His6."

Following transformation with the pET-30a(+)-prsA-His6 vector by heat shock, *E. coli* DH5α was incubated at 37° C. for 1 hr in 1 mL of LB broth, and grown at 37° C. for 16 hrs on LB agar plates containing kanamycin. Of the colonies formed on the plates, one was picked, and examined by colony-PCR and restriction enzyme mapping with regard to whether it contained pET-30a(+)-prsA-His6. The plasmid was amplified and prepared from the bacteria, and transformed into *E. coli* BL21 by heat shock. The transformed *E. coli* was incubated at 37° C. for 1 hr in 1 mL of LB broth, and grown at 37° C. for 16 hrs on LB agar plates containing kanamycin. One of the colonies thus formed was inoculated into 5 mL of LB broth, and grown at 37° C. to $O.D_{600}$=0.4 at which the cells were induced at 37° C. for 3 hrs in the presence of 1 mM IPTG to overexpress the fusion protein.

From the Gram-negative bacterium *E. coli* that had been transformed with the pET-30a(+)-prsA-His6 vector or that had not been transformed, microvesicles loaded with the Histag fusion protein, or unloaded microvesicles, were constructed using the methods disclosed in Examples 1 and 2. Thereafter, 20 μg of each of the microvesicles was individually mixed with such an amount of a 5× loading dye that the concentration of the loading dye was diluted 1×. The mixtures were boiled at 100° C. for 5 min, and loaded into a 12% polyacrylamide gel. After electrophoresis at 80 V for 2 hrs, the proteins were transferred onto a PVDF membrane at 400 mA for 2 hrs. The membrane was blocked at 4° C. for 12 hrs in a 3% solution of skim milk in PBS. The membrane was treated at room temperature for 2 hrs with an anti-His-tag antibody, washed twice with PBS, and reacted at room temperature for 1 hr with a peroxidase-conjugated secondary antibody. It was washed again for 30 min with PBS, followed by visualization with an ECL substrate. The result is shown in FIG. 32.

Figure 32:
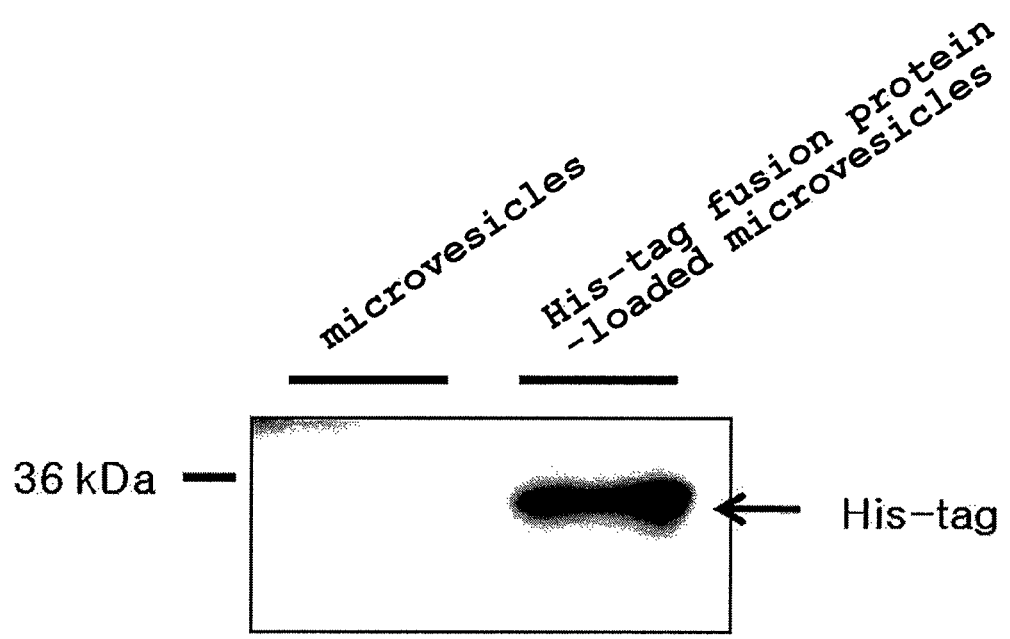
FIG. 32 is a view showing a His-tag fusion protein loaded to protoplast-derived microvesicles.

As can be seen in FIG. 32, the microvesicles constructed from the protoplast of the His-tag fusion protein-overexpressing bacteria were detected by an anti-His-tag antibody, whereas the His-tag protein was not detected in the microvesicles constructed from the protoplast of bacteria void of the His-tag fusion protein.

From the result, it is apparent that microvesicles loaded with the His-tag fusion protein were constructed correctly.

Example 22

In Vitro Drug Delivery of Bacterial Protoplast-Derived Microvesicles and Induction of Cell Death of Vascular Endothelial Cells In 6-well plates was placed the cover glass coated with 0.1% gelatin to which HUVEC was then seeded at a density of 1×10⁵ cells/cover glass, followed by incubation for 16 hrs. The cells were washed twice with PBS, and incubated for 24 hrs in 2 mL of a medium per well containing the Gram-negative bacterial protoplast-derived microvesicles, prepared in Examples 1 and 2, or the Gram-negative bacterial protoplast-derived microvesicles loaded with doxorubicin, prepared in Example 17, at concentrations of 0, 0.5, 1, or 2 μg/ml. Again, the cells were washed with PBS, and 2 mL of a serum-free medium was added to each well before incubation for 30 min with 5 μM Cell Tracker. Again, the cells were washed with PBS, and incubated for 30 min in 2 mL of a serum-supplemented medium in each well. The cover glass was fixed for 10 min with 2 mL of 4% paraformaldehyde in each well and observed under a confocal microscope. Living cells were counted, and the results are given in FIG. 33.

Figure 33:
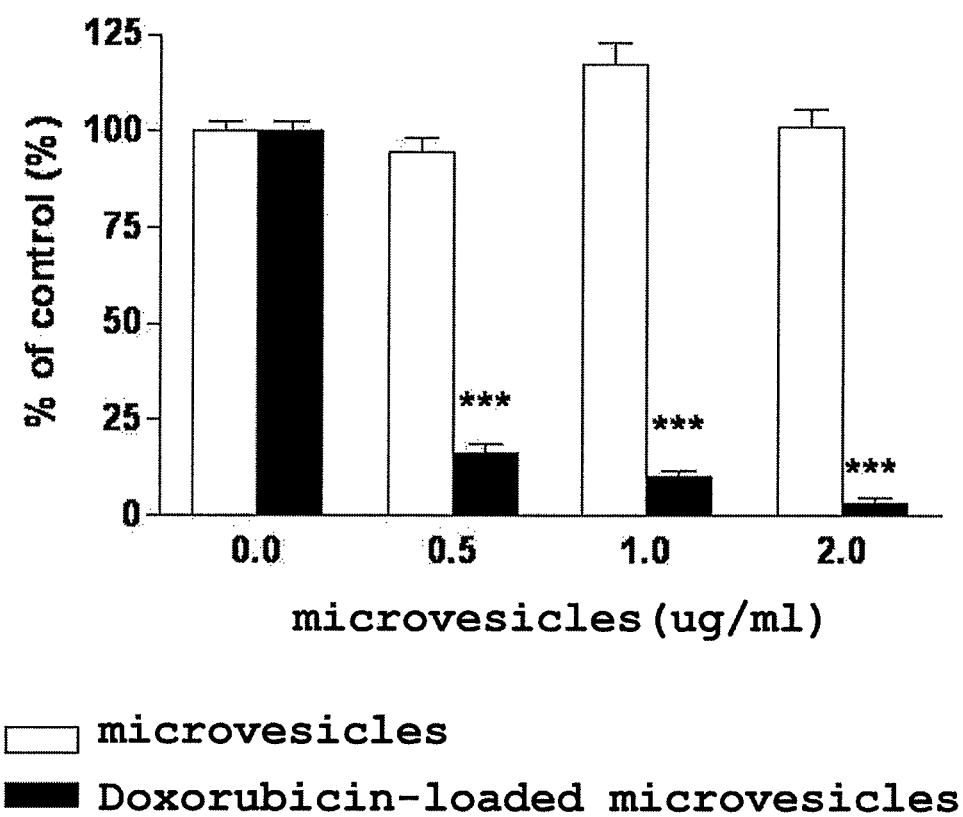
FIG. 33 is graph showing the induction of cell death in vascular endothelial cells by protoplast-derived microvesicles loaded with doxorubicin.

In FIG. 33, "% of control" on the Y-axis represents a percentage of the count of the cells alive upon treatment with the microvesicles at each concentration, relative to the count of the cells alive upon treatment with the microvesicle at a concentration of 0 μg/ml, as calculated by the following equation:

$$\% \text{ of control} = \frac{\text{Counts of Living Cells at each concentration}}{\text{Counts of Living Cells at 0 } \mu g/ml} \times 100$$

A higher percentage of control at a given concentration means less induction of cell death, compared to the control, that is, at 0 μg/ml As can be seen in FIG. 33, microvesicles themselves derived from bacterial protoplasts had no influences on the death of HUVEC cells, wherein the doxorubicin-loaded microvesicles derived from bacterial protoplasts induced HUVEC cells to experience cell death.

These results demonstrate that the doxorubicin loaded to the protoplast-derived microvesicles was delivered to HUVEC cells and induced them to undergo cell death.

Example 23

In Vitro Induction of Cell Death in Colon Cancer by Bacterial Protoplast-Derived, Doxorubicin-Loaded Microvesicles In 24-well plates was placed the cover glass coated with 0.1% gelatin to which mouse colon 26 cell line was then seeded at a density of 2×10⁴ cells/cover glass, followed by incubation for 16 hrs.

The cells were washed twice with PBS, and incubated for 24 hrs in 500 μl of a medium per well containing the Gram-positive bacterial protoplast-derived microvesicles, prepared according to the methods of Examples 1 and 2, or the Gram-positive bacterial protoplast-derived microvesicles loaded with doxorubicin, prepared according to the method of Example 17, at concentrations of 0, 1.25, 2.5, or 5 μg/ml.

Again, the cells were washed with PBS, and 500 μl of a serum-free medium was added to each well before incubation for 30 min with 5 μM Cell Tracker. Again, the cells were washed with PBS, and incubated for 30 min in 500 μl of a serum-supplemented medium in each well. The cover glass was fixed for 10 min with 500 μl of 4% paraformaldehyde in each well and observed under a confocal microscope. Living cells were counted, and the results are given in FIG. 34.

Figure 34:
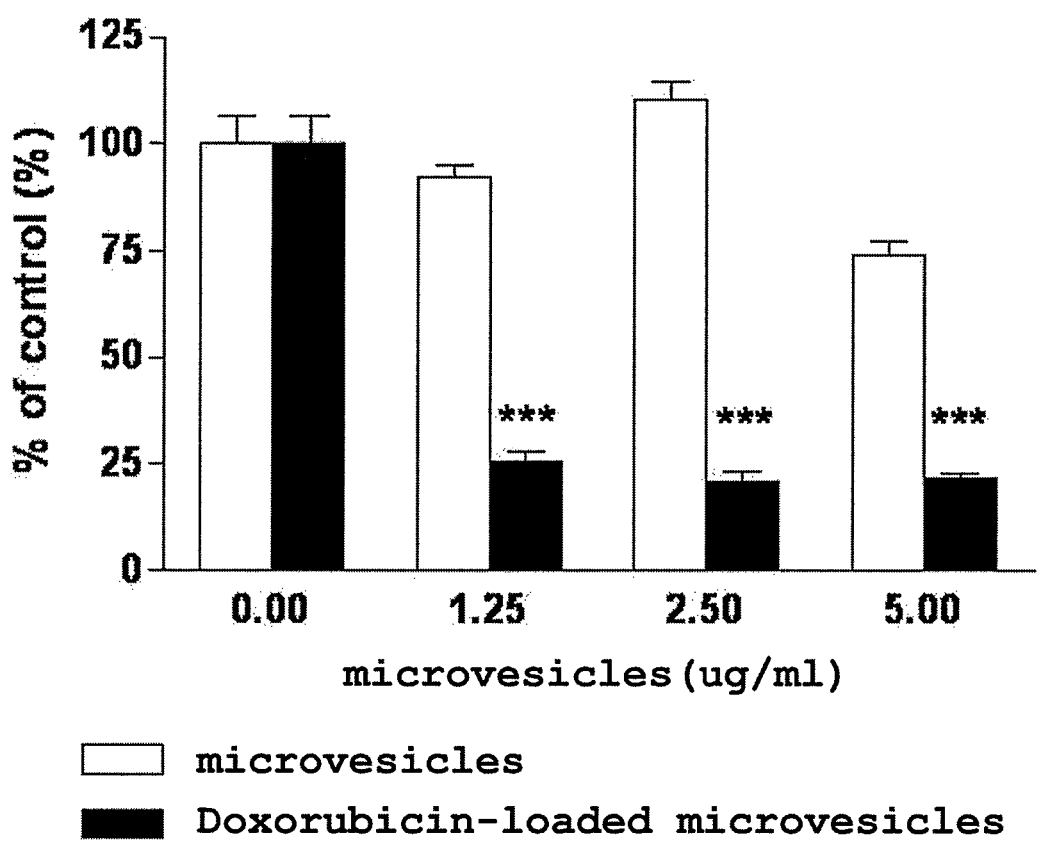
FIG. 34 is a graph showing the induction of cell death in mouse colon cells by protoplast-derived microvesicles loaded with doxorubicin.

In FIG. 34, counts of the cells alive upon treatment with the microvesicles at given concentrations are expressed as percentages of the control, that is, the count of the cells alive upon treatment with the microvesicle at a concentration of 0 μg/ml, as calculated by the following Equation:

$$\% \text{ of control} = \frac{\text{Counts of Living Cells at each concentration}}{\text{Counts of Living Cells at 0 } \mu g/ml} \times 100$$

As can be seen in FIG. 34, doxorubicin-loaded, protoplast-derived microvesicles very effectively induced colon cancer cells to undergo cell death, compared to unloaded, protoplast-derived microvesicles themselves.

From these results, it is apparent that the doxorubicin loaded to the protoplast-derived microvesicles was delivered to colon cancer cells and induced them to undergo cell death.

Example 24

In Vivo Induction of Cell Death in Cancer by Doxorubicin-Loaded, Bacterial Protoplast-Derived Microvesicles Mouse colon 26 cell line was subcutaneously injected at a dose of $1\times10^6$ cells into mice, and cultured for 5 days. Thereafter, a PBS solution containing 0 μg, 1 μg, or 5 μg of the doxorubicin-loaded, Gram-negative bacterial protoplast-derived microvesicles, prepared in Example 17, was injected at a dose of 100 μl twice a week via the tail vein into mice. The sizes of cancer tissue were monitored and the results are given in FIG. 35. The volume of cancer tissue was calculated by the equation $v=ls^2/2$, wherein l is a length of the longest axis of a tumor and s is a length of the axis perpendicular to the longest axis.

Figure 35:
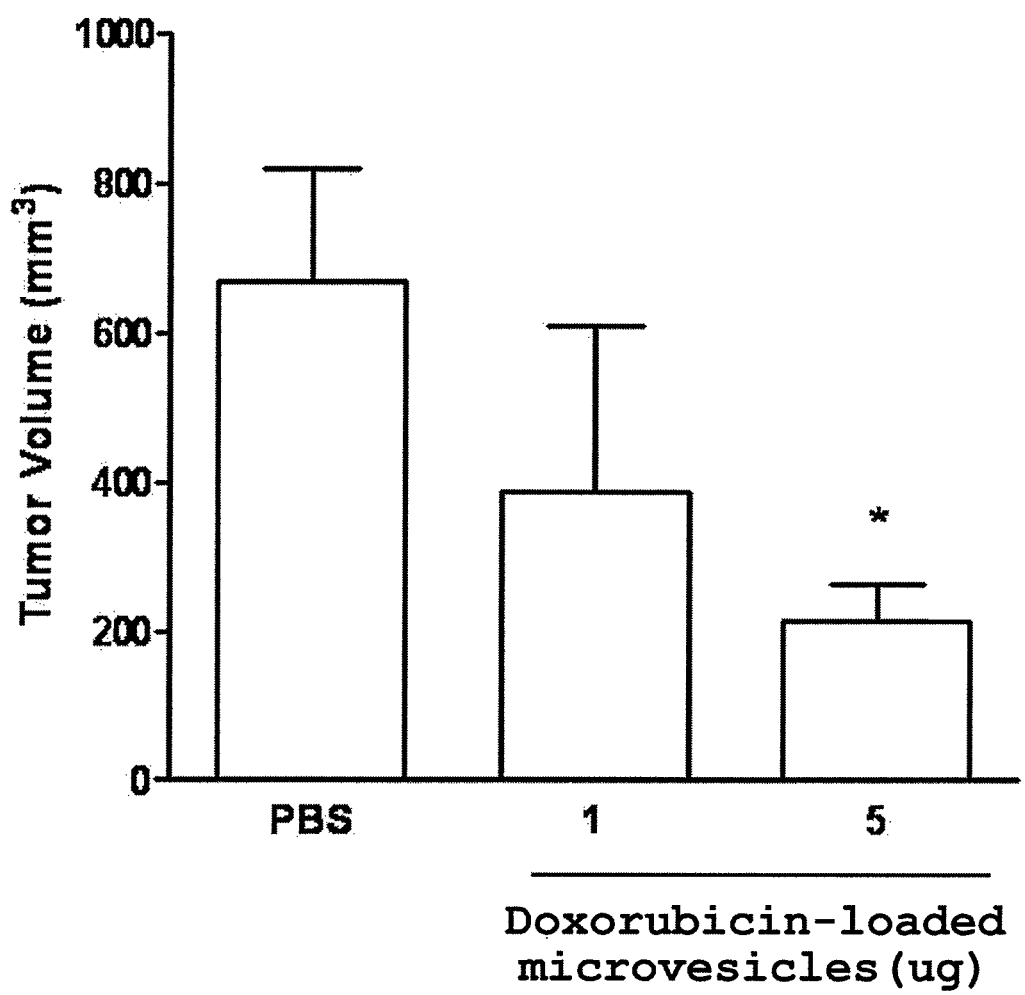
FIG. 35 is a graph showing the inhibition of doxorubicin-loaded, protoplast-derived microvesicles against the growth of cancer tissues in mice.

As can be seen in FIG. 35, lower cancer growth was found in mice injected with doxorubicin-loaded microvesicles compared to mice injected with PBS only, with the smallest cancer tissue detected at a dose of 5 μg of the doxorubicin-loaded microvesicles.

This result indicates that the anticancer drug doxorubicin can be delivered to cancer tissues by the protoplast-derived microvesicles.

Although certain embodiments of the present invention have been disclosed for illustrative purposes, those skilled in the art will appreciate that various modifications, additions and substitutions are possible, without departing from the scope and spirit of the invention as disclosed in the accompanying claims.

Being derived from protoplasts constructed by removing the cell wall from bacteria, archaea, fungi, or plant cells, the microvesicles of some embodiments of the present invention do not trigger an immune response by themselves. Further, the protoplast-derived microvesicles are advantageous in that they can be readily loaded with a therapeutic and/or diagnostic substance, or a vaccine substance, and can be produced on a mass scale. Moreover, if the microvesicles are derived from the protoplast of a cell expressing the therapeutic, the diagnostic, and/or the vaccine substance, they have industrial and economic advantages because they can be produced without purifying the substance.

What is claimed is:

1. A method of making a pharmaceutical composition, the method comprising:
   providing bacteria comprising a cell wall, an antigenic protein and an extracellular domain;
   removing the cell wall from the bacteria to provide a cell-wall-deficient composition that is deficient of the cell wall and comprises the antigenic protein and the extracellular domain;
   processing the cell-wall-deficient composition to produce microvesicles comprising the antigenic protein and the extracellular domain, wherein the resulting microvesicles comprise a mixture of first type microvesicles with the extracellular domain on their outer surfaces and second type microvesicles with the extracellular domain on their inner surfaces;
   isolating, from the mixture, at least part of the first type microvesicles with the extracellular domain on their outer surfaces; and
   formulating a pharmaceutical composition comprising the isolated microvesicles with the extracellular domain on their outer surfaces.

2. The method of claim 1, wherein the bacteria comprise Gram-positive bacteria.

3. The method of claim 1, wherein the bacteria comprise Gram-negative bacteria.

4. The method of claim 1, wherein the bacteria comprise at least one selected from the group consisting of *Escherichia coli* and *Staphylococcus aureus*.

5. The method of claim 1, wherein the isolated microvesicles comprise one or more non-native chemical entities chemically bonded to at least part of membrane components thereof, wherein the one or more non-native chemical entities are selected from the group consisting of a non-native molecule comprising a thiol (—SH) group, a non-native molecule comprising an amine (—NH$_2$) group, a non-native targeting molecule, a fusogen, and polyethylene glycol.

6. The method of claim 1, wherein the antigenic protein is selected from the group consisting of a viral protein, a pathogenic bacterial protein and a cancer cell-derived protein.

7. The method of claim 6, wherein the viral protein is from at least one virus selected from the group consisting of immunodeficiency virus (HIV), human papilloma virus (HPV), hepatitis B virus (HBV), hepatitis C virus (HCV) and influenza virus.

8. The method of claim 6, wherein the pathogenic bacterial protein is from at least one bacterium selected from the group consisting of *Enterobacter aerogenes, Enterobacter cloacae, Staphylococcus aureus, Klebsiella pneumonia, Acinetobacter baumannii, Pseudomonas aeruginosa,* and *Enterococcus faecalis*.

9. The method of claim 1, wherein the pharmaceutical composition further comprises at least one additional antigenic entity selected from the group consisting of a lipid molecule from a virus, a lipid molecule from a pathogenic bacteria, a carbohydrate molecule from a virus and a carbohydrate molecule from a pathogenic bacteria.

10. The method of claim 1, wherein the pharmaceutical composition further comprises at least one of an immunopotentiator and an immunomodulator.

11. The method of claim 10, wherein the immunopotentiator comprises one or more selected from the group consisting of double-stranded RNA (dsRNA), a cholera toxin, and alum.

12. The method of claim 10, wherein the immunomodulator comprises one or more selected from the group consisting of interleukin (IL)-2, IL-4, IL-6, IL-12, IL-17, interferon gamma (IFN-gamma), vascular endothelial growth factor (VEGF), and fibroblast growth factor (FGF)-2.

13. The method of claim 1, wherein the pharmaceutical composition further comprises at least one additional protein configured to target specific cells or tissues in the subject.

14. The method of claim 13, wherein the at least one additional protein is selected from the group consisting of a cell adhesion molecule, an antibody, a targeting protein, a cell membrane fusion protein and any fusion proteins of two or more the foregoing.

15. The method of claim 13, wherein the at least one additional protein is selected from the group consisting of a protein for ligand display, a peptide for ligand display, a protein for a ligand trap, a peptide for a ligand trap, and a fusion protein of two or more of the foregoing.

16. The method of claim 1, wherein the antigenic protein is a non-native protein of the bacteria as the bacteria are transformed with a gene for encoding the antigenic protein.

17. The method of claim 1, wherein the antigenic protein and the extracellular domain are connected to form a fusion protein, wherein the bacteria are transformed with a gene for encoding the fusion protein.

18. The method of claim 17, wherein the fusion protein further comprises a cytoplasmic domain connected to the extracellular domain, wherein the first type microvesicles comprise the cytoplasmic domain on their inner surfaces and the second type microvesicles comprise the cytoplasmic domain on their outer surfaces, wherein isolating comprises:
   adding, to the mixture, an antibody configured to bind with the cytoplasmic domain such that the second type microvesicles bind with the antibody; and
   removing the second type microvesicles bound with the antibody.

19. The method of claim 1, wherein the pharmaceutical composition comprises a vaccine composition for causing an immune response to the antigenic protein.

* * * * *

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial sequence
<220> FEATURE:
<223> OTHER INFORMATION: Forward primer

<400> SEQUENCE: 1
ggaattccat atggtgagca agggcgagga                                        30

<210> SEQ ID NO 2
<211> LENGTH: 31
<212> TYPE: DNA
<213> ORGANISM: Artificial sequence
<220> FEATURE:
<223> OTHER INFORMATION: Reverse primer

<400> SEQUENCE: 2
acgcgtcgac ttacttgtac acctcgtcca t                                      31

<210> SEQ ID NO 3
<211> LENGTH: 31
<212> TYPE: DNA
<213> ORGANISM: Artificial sequence
<220> FEATURE:
<223> OTHER INFORMATION: Forward primer

<400> SEQUENCE: 3
ggaattccat atgggtgagc aagggcgagg a                                      31

<210> SEQ ID NO 4
<211> LENGTH: 31
<212> TYPE: DNA
<213> ORGANISM: Artificial sequence
<220> FEATURE:
<223> OTHER INFORMATION: Reverse primer
```

<400> SEQUENCE: 4
aggcgtcgac ttacttgtac agctcgtcca t                            31

<210> SEQ ID NO 5
<211> LENGTH: 25
<212> TYPE: DNA
<213> ORGANISM: Artificial sequence
<220> FEATURE:
<223> OTHER INFORMATION: Forward primer

<400> SEQUENCE: 5
ggaattccat atgccccaag aagac                                    25

<210> SEQ ID NO 6
<211> LENGTH: 25
<212> TYPE: DNA
<213> ORGANISM: Artificial sequence
<220> FEATURE:
<223> OTHER INFORMATION: Reverse primer

<400> SEQUENCE: 6
aggcgtcgac tcagggtgaa taagg                                    25

<210> SEQ ID NO 7
<211> LENGTH: 25
<212> TYPE: DNA
<213> ORGANISM: Artificial sequence
<220> FEATURE:
<223> OTHER INFORMATION: Forward primer

<400> SEQUENCE: 7
catatgaaga aaatcgcaat agcag                                    25

<210> SEQ ID NO 8
<211> LENGTH: 29
<212> TYPE: DNA
<213> ORGANISM: Artificial sequence
<220> FEATURE:
<223> OTHER INFORMATION: Reverse primer

<400> SEQUENCE: 8
tctagattta gaattgcttg aagatgaag                                29

<210> SEQ ID NO 9
<211> LENGTH: 29
<212> TYPE: DNA
<213> ORGANISM: Artificial sequence
<220> FEATURE:
<223> OTHER INFORMATION: Forward primer

<400> SEQUENCE: 9
gctctagaaa tactgactct gaatgtccc                                29

<210> SEQ ID NO 10
<211> LENGTH: 29
<212> TYPE: DNA
<213> ORGANISM: Artificial sequence
<220> FEATURE:
<223> OTHER INFORMATION: Reverse primer

<400> SEQUENCE: 10
caagctttca gcgcagttcc caccacttc                                29

```
<210> SEQ ID NO 11
<211> LENGTH: 30
<212> TYPE: DNA
<213> ORGANISM: Artificial sequence
<220> FEATURE:
<223> OTHER INFORMATION: Forward primer

<400> SEQUENCE: 11
gcctctagac tggaggaaaa gaaagtttgc                              30

<210> SEQ ID NO 12
<211> LENGTH: 26
<212> TYPE: DNA
<213> ORGANISM: Artificial sequence
<220> FEATURE:
<223> OTHER INFORMATION: Reverse primer

<400> SEQUENCE: 12
ccaagcttca ggacgggatc ttaggc                                  26
```